(12) United States Patent
Baxter-Jones et al.

(10) Patent No.: US 6,524,259 B2
(45) Date of Patent: Feb. 25, 2003

(54) DEVICES AND METHODS FOR CERVIX MEASUREMENT

(75) Inventors: Rosalyn P. Baxter-Jones, San Diego, CA (US); Joseph Stemler, Corona Del Mar, CA (US); Lindy Yow, Costa Mesa, CA (US)

(73) Assignee: Cervilenz, Inc., Irvine, CA (US)

( * ) Notice: Subject to any disclaimer, the term of this patent is extended or adjusted under 35 U.S.C. 154(b) by 0 days.

(21) Appl. No.: 09/877,986

(22) Filed: Jun. 8, 2001

(65) Prior Publication Data

US 2002/0198471 A1 Dec. 26, 2002

(51) Int. Cl.$^7$ .......................... A61B 5/103; A61B 5/117
(52) U.S. Cl. ........................................ 600/591; 600/587
(58) Field of Search .................... 600/588, 589, 600/590, 591, 587

(56) References Cited

U.S. PATENT DOCUMENTS

| | | | |
|---|---|---|---|
| 3,630,190 A | 12/1971 | Baker ............................ 128/2 |
| 3,706,307 A | * 12/1972 | Hasson ........................ 600/591 |
| 4,016,867 A | 4/1977 | King et al. ..................... 128/2 |
| 4,224,951 A | 9/1980 | Hasson ........................ 128/778 |
| 4,248,214 A | * 2/1981 | Hannah et al. ................ 604/20 |
| 4,489,732 A | * 12/1984 | Hasson ........................ 33/512 |
| 4,500,313 A | * 2/1985 | Young .......................... 600/587 |
| 4,685,474 A | 8/1987 | Kurz et al. ................... 128/778 |
| 5,657,764 A | * 8/1997 | Coulter et al. ............... 600/591 |
| 5,658,295 A | 8/1997 | Krementsov ................. 606/119 |
| 5,980,804 A | 11/1999 | Koch .......................... 264/222 |
| 6,039,701 A | 3/2000 | Sliwa et al. ................. 600/588 |

OTHER PUBLICATIONS

Rush et al., "Contribution or preterm delivery to perinatal mortality." British Medical Journal 2:965–968 (1976).

Villar et al., "Pre-term delivery syndrome: the unmet need." Res. Clin. Forums 16(3):9–33 (1994).

Anderson et al., "Prediction of risk for preterm delivery by ultrasonographic measurement of cervical length." Am. J. Obstet. Gynecol. 163(3):859–867 (1990).

Iams et al., "The length of the cervix and the risk of spontaneous premature delivery." N. Eng. J. Med. 334(9):567–72 (1996).

Health et al., "Cervical length at 23 weeks of gestation: prediction of spontaneous preterm delivery." Ultrasound Obstet. Gynecol. 12:312–317 (1998).

Sonek et al., "Preterm Birth, Causes, Prevention and Management." Second Edition, chapter 5, McGraw-Hill, Inc. pp. 137–160 (1993).

Michaels et al. "Ultrasound differentiation of the competent from the incompetent cervix: Prevention of preterm delivery." Am. J. Obstet Gynecol. 154(3):537–546 (1986).

Sarti et al. "Ultrasonic Visualization of a Dilated Cervix During Pregnancy." Radiology 130:417–420 (1979).

Vaalamo and Kivikoski, "The incompetent Cervix During Pregnancy Diagnosed by Ultrasound." Acta Obstet. Gynecol Scand 62:19–21 (1983).

(List continued on next page.)

*Primary Examiner*—Timothy L. Maust
(74) *Attorney, Agent, or Firm*—O'Melveny & Myers LLP

(57) ABSTRACT

Devices and methods for determining dimensions of female reproductive organs. In one embodiment, a device for determining a dimension of a female reproductive organ includes a hollow member having a distal end, a proximal end, and a lumen, a measurement member insertable into the lumen of the hollow member and having a distal portion, a proximal portion, and a measurement scale disposed along the proximal portion, a substantially translucent flange attached to the distal end of the hollow member and having a body offset from the hollow member, an opening for advancement of the measurement member there through, and a measurement scale on the body, and a light element placed within the distal portion of the measurement member.

11 Claims, 8 Drawing Sheets

OTHER PUBLICATIONS

Anderson et al., "Relationship between length of gestation and cervical dilatation, uterine contractility, and other factors during pregnancy." Am. J. Obst. & Gynec. 105(8):1207–1214 (1969).

Phillip G. Stubblefield, "Preterm Birth, Causes, Prevention, and Management." Second Edition, Chapter 1, pp. 3–39, McGraw–Hill, Inc. (1993).

Wood et al., "The prediction of premature labor by observation of the cervix and external tocography." Am. J. Obst. & Gynec. 91(3):396–402 (1965).

Nzeh and Adetoro, "Sonographic assessment of the incompetent cervix in pregnancy." Int. J. Gynecol. Obstet. 37:179–184 (1992).

Norwitz et al., "The Control of Labor." New Eng. J. of Med. 341(9):660–666 (1999).

Phillip G. Stubblefield, M.D., "Preterm Birth: Causes, Prevention, and Management, Cervical Incompetence", Chapter 6, pp. 98–111 (1984).

I. Brook et al., Ultrasonography in the Diagnosis of Cervical Incompetence in Pregnancy–A New Diagnostic Approach, British Journal of Obstetrics and Gynecology, Jun. 1981, vol. 88, pp. 640–643.

\* cited by examiner

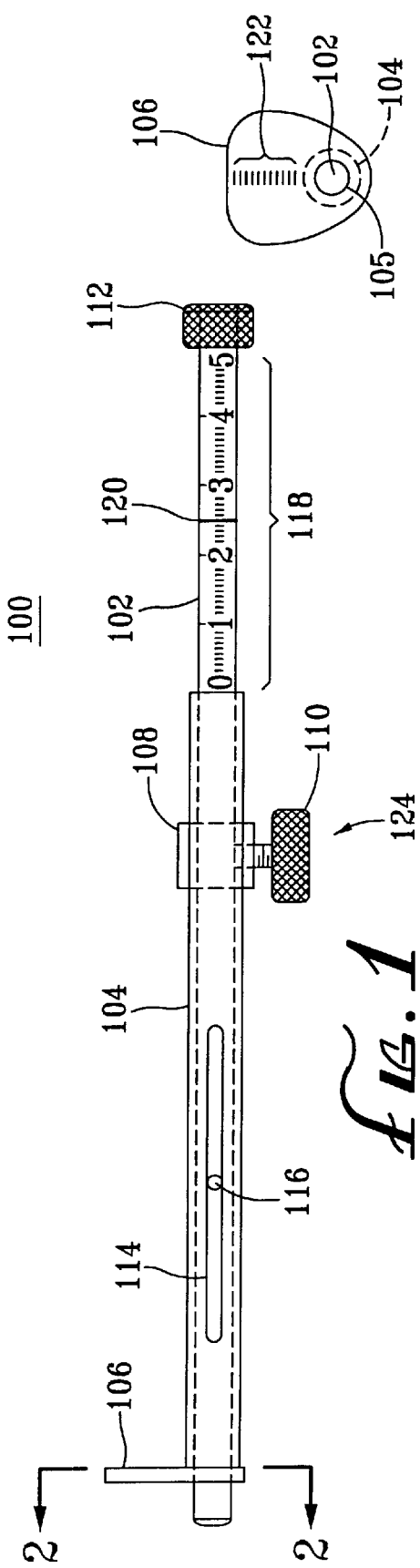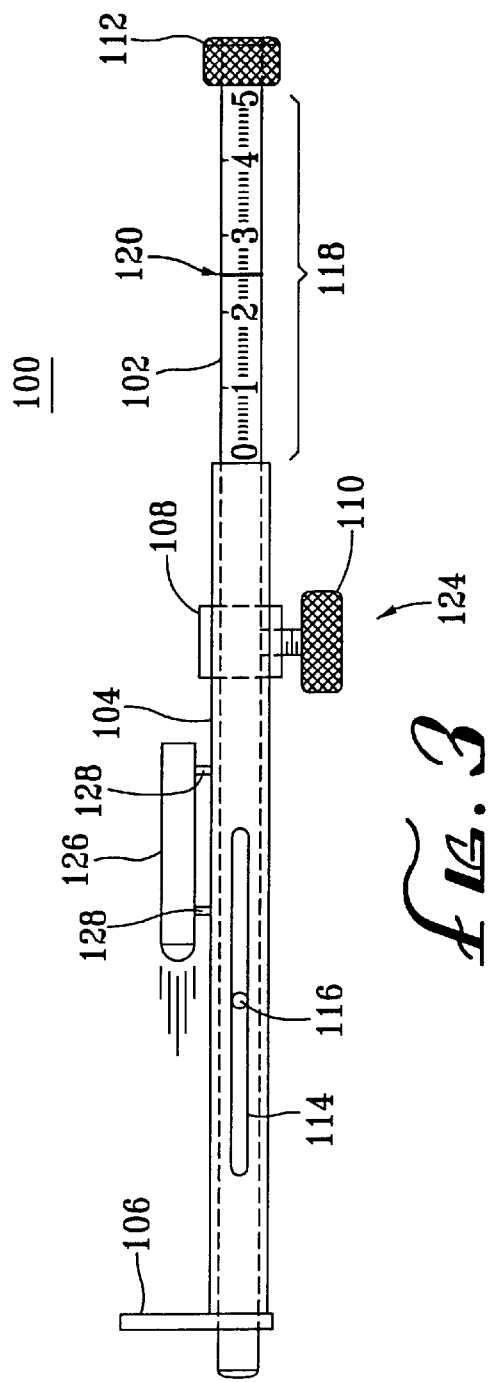

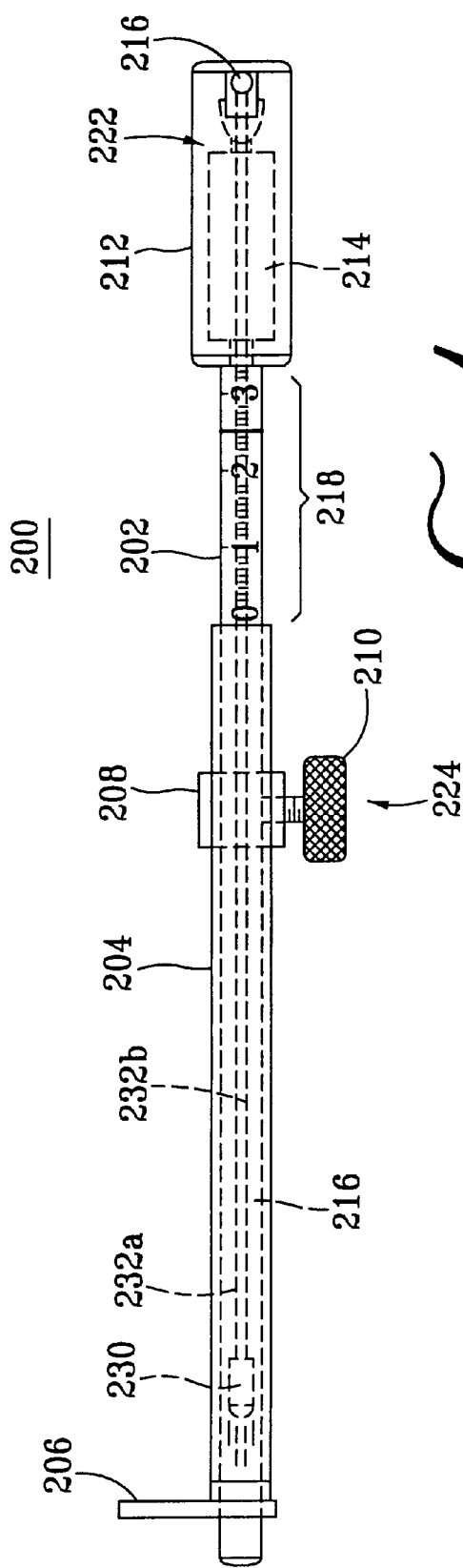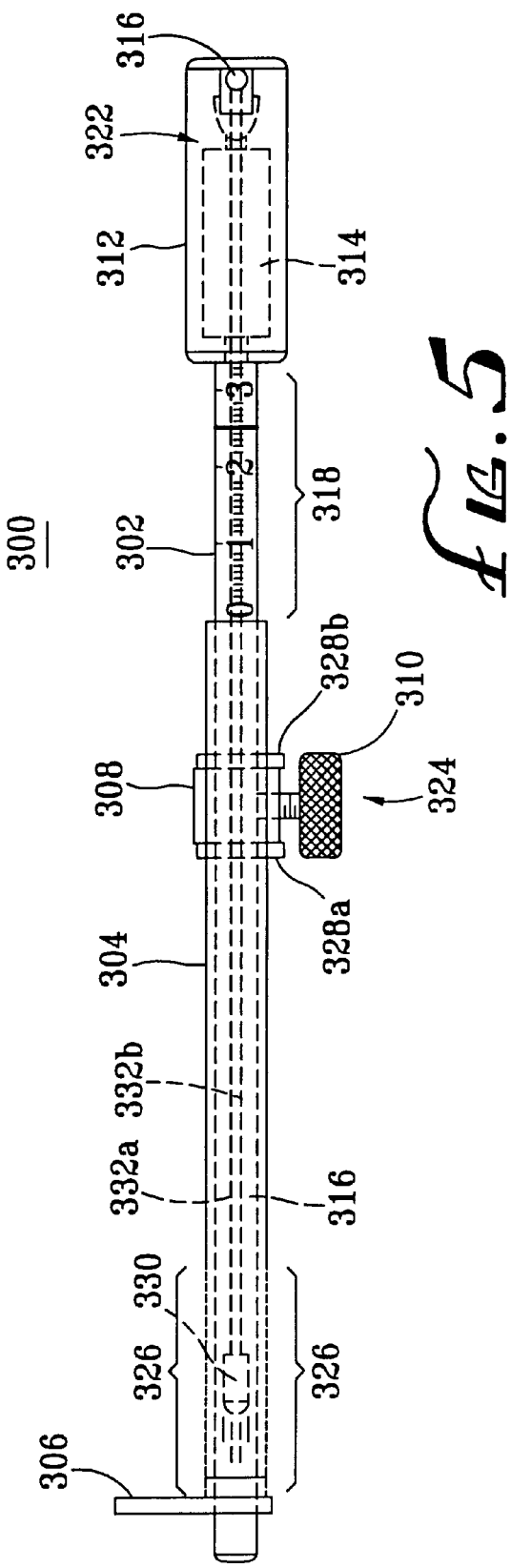

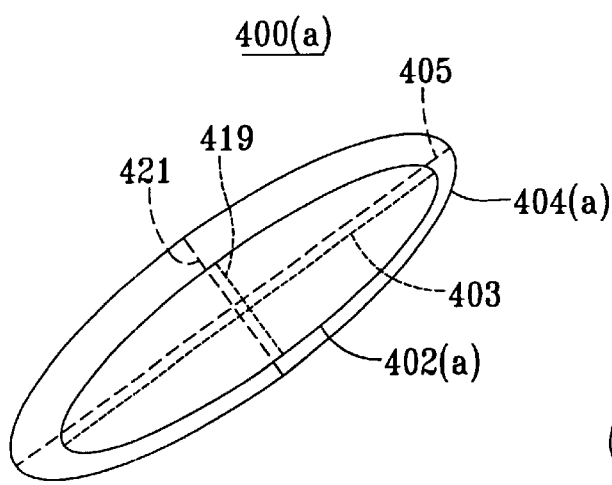
FIG. 6a(i)
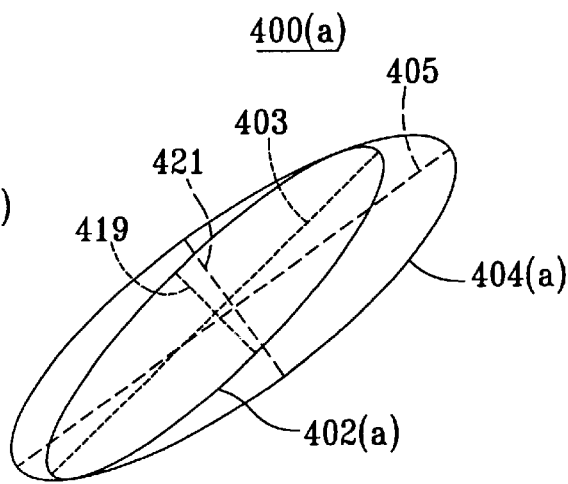
FIG. 6a(ii)
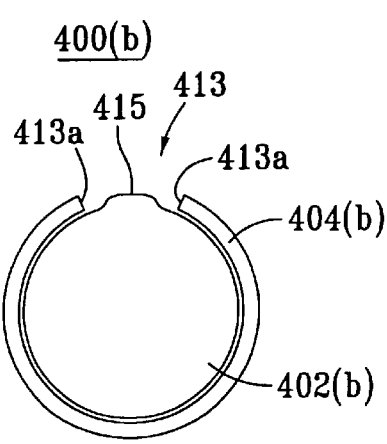
FIG. 6b
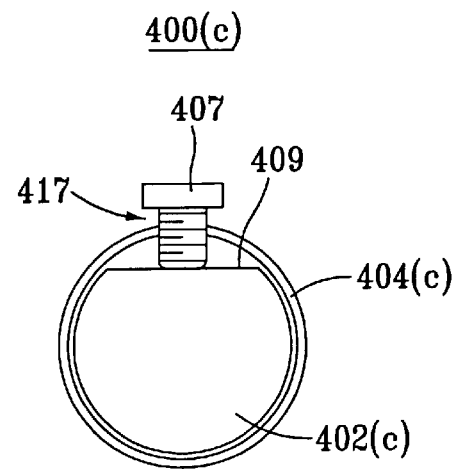
FIG. 6c

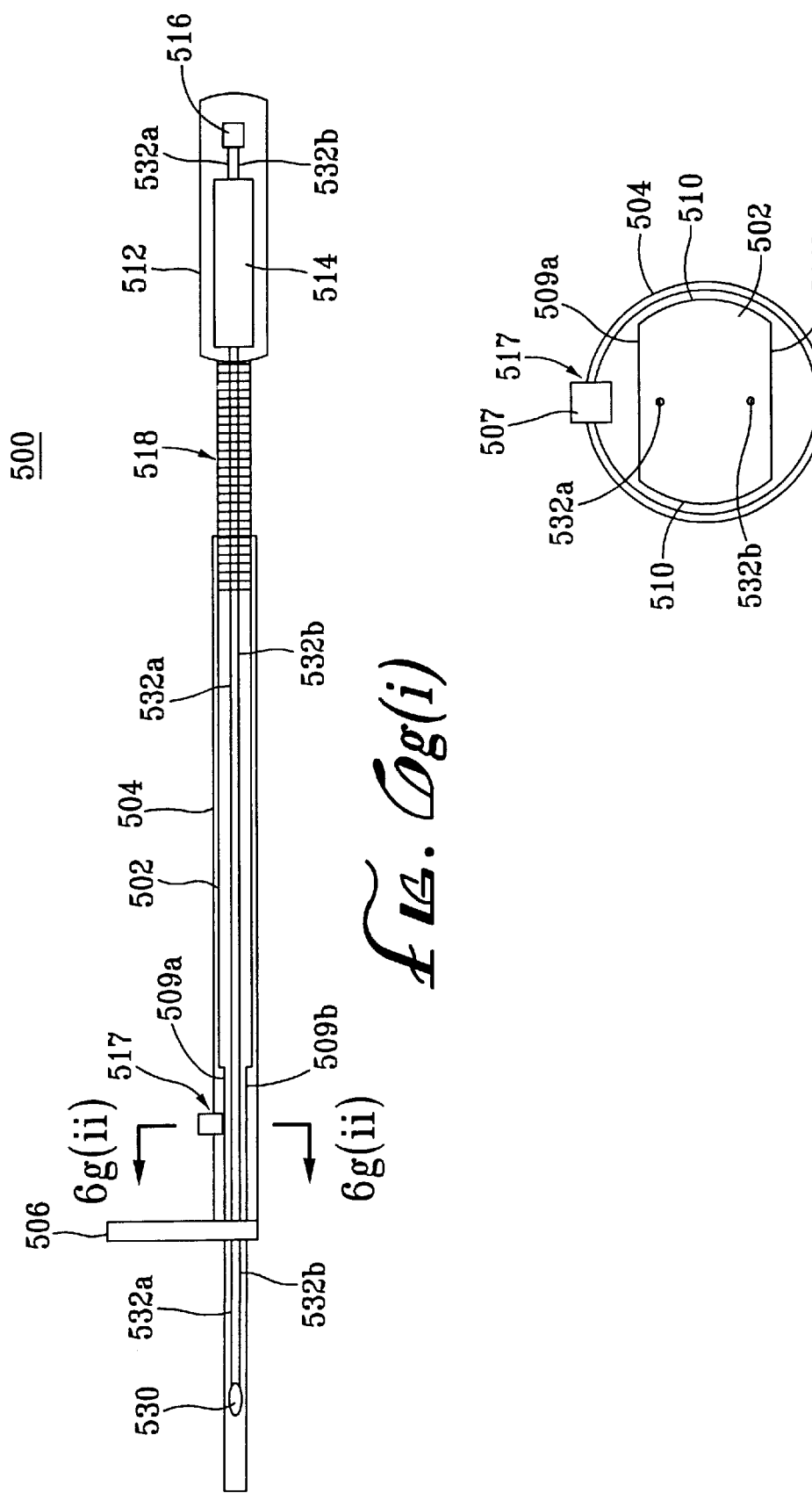

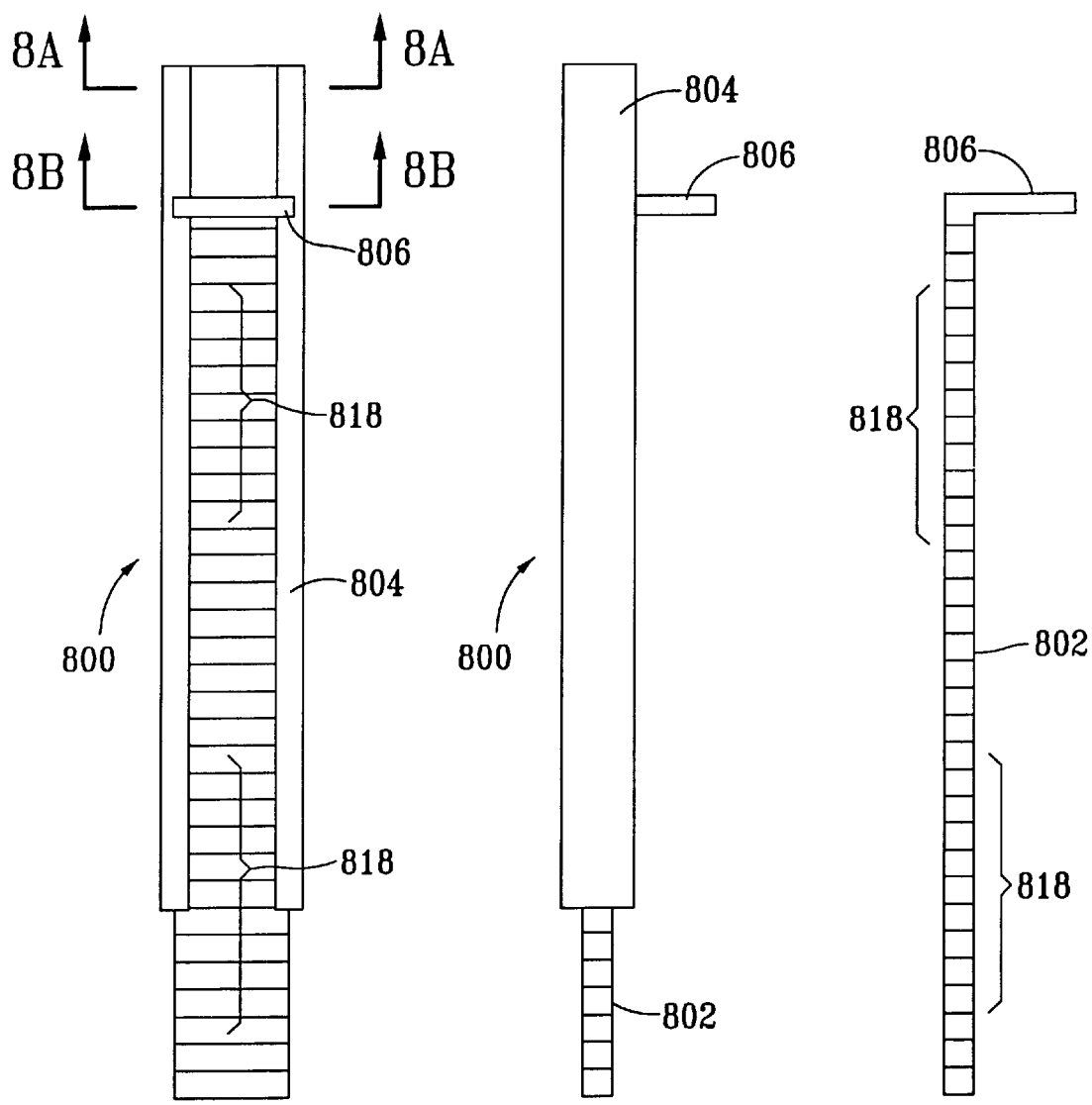
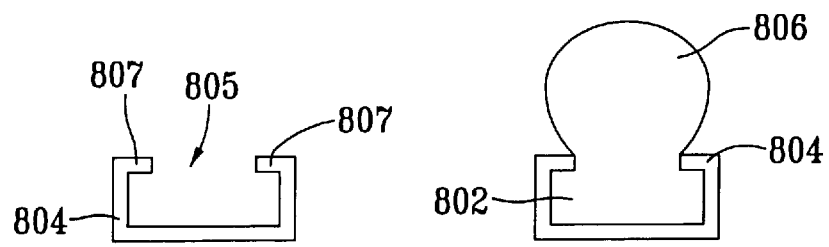
FIG. 8  FIG. 8C  FIG. 8D
FIG. 8A  FIG. 8B

DEVICES AND METHODS FOR CERVIX MEASUREMENT

FIELD OF THE INVENTION

The present invention relates to medical devices and methods of using such devices. More particularly, the invention relates to instruments and methods to measure the length of the cervix in the fornix vaginae and the dilation of the cervix uteri.

BACKGROUND

Preterm labor, or labor before 37 weeks gestation, has been reported in 7 to 10 percent of all births but accounts for more than 85 percent of all perinatal complications and death. Rush et al., BMJ 2:965–8 (1976) and Villar et al., Res. Clin. Forums 16:9–33 (1 994), which are both incorporated herein by reference. An inverse relationship between cervical length in the fornix vaginae and the risk of preterm labor has also been observed. Anderson et al., Am. J. Obstet. Gynecol. 163:859 (1990); Iams et al., N. Eng. J. Med. 334:567–72 (1996) and Heath et al., and Ultrasound Obstet. Gynecol. 12:312–7 (1998), which all are incorporated herein by reference. Accordingly, many physicians find it useful to examine the cervix in the fornix vaginae as part of normal prenatal care in order to assess risk of preterm labor.

It has long been known that the cervix normally undergoes a series of physical and biochemical changes during the course of pregnancy, which enhance the ease and safety of the birthing process for the mother and baby. For example, in the early stages of labor the tissues of the cervical canal soften and become more pliable, the cervix shortens (effaces), and the circumference of the proximal end of the cervical canal begins to increase at the internal os. As labor progresses, growth of the cervical diameter propagates to the distal end of the cervical canal, toward the external os. In the final stages of labor, the external os dilates allowing for the unobstructed passage of the fetus.

In addition to the physical and biochemical changes associated with normal labor, genetic or environmental factors, such as medical illness or infection, stress, malnutrition, chronic deprivation and certain chemicals or drugs can cause changes in the cervix. For example, it is well known that the in utero exposure of some women to diethylstilbestrol (DES) results in cervical abnormalities and in some cases gross anatomical changes, which leads to an incompetent cervix where the cervix matures, softens and painlessly dilates without apparent uterine contractions. An incompetent cervix can also occur where there is a history of cervical injury, as in a previous traumatic delivery, or as a result of induced abortion of the cervix is forcibly dilated to large diameters, Details of the incompetent cervix are discussed in Sonek, et al., Preterm Birth, Causes, Prevention and Management, Second Edition, McGraw-Hill, Inc., (1993), Chapter 5, which is incorporated by reference herein.

Cervical incompetence is a well recognized clinical problem. Several investigators have reported evidence of increased cervical os diameter as being consistent with cervical incompetence (see Brook et al., J. Obstet. Gynecol. 88:640 (1981); Michaels et al., Am. J. Obstet. Gynecol. 154:537 (1986); Sarti et al., Radiology 130:417 (1979); and Vaalamo et al., Acta Obstet. Gynecol. Scan 62:19 (1983), all of which are incorporated by reference herein). Internal os diameters ranging between 15 mm to 23 mm have been observed in connection with an incompetent cervix. Accordingly, a critical assessment in the diagnosis of an incompetent cervix involves measurement of the internal cervical os diameter.

There are also devices and methods to measure the diameter of the external cervical os. For example, cervical diameter can be manually estimated by a practitioner's use of his or her digits. Although an individual practitioner can achieve acceptable repeatability using this method, there is significant variation between practitioners due to the subjective nature of the procedure. To address these concerns, various monitoring and measuring devices and methods have been developed. For example, an instrument for measuring dilation of the cervix uteri is described in U.S. Pat. No. 5,658,295. However, this device is somewhat large, leading to a risk of injury to the fundus of the vagina or cervical os. Additionally, it is not disposable and requires repeated sterilization. Another device for measuring cervical diameter is described, for example, in U.S. Pat. No. 6,039, 701. In one version, the device described therein has a loop element which is secured to the cervix. The loop expands or contracts with the cervix and a gauge is coupled to the loop for measuring changes in the loop dimension. Such changes can then be detected by electronic means. Accordingly, this device is rather complex and expensive to manufacture.

Even if a woman is found to have an apparently normal internal cervical os diameter, there may nonetheless be a risk for preterm labor and delivery. Currently, risk assessment for preterm delivery remains difficult, particularly among women with no history of preterm birth. However, the findings that preterm delivery is more common among women with premature cervical shortening or effacement suggest that measuring the length of the cervix would be predictive for preterm labor.

Currently, a physician has at least two options to measure the length of the cervix in the fornix vaginae. One such method involves serial digital examination of the cervix by estimating the length from the external cervical os to the cervical-uterine junction, as palpated through the vaginal fornix. Although this is useful for general qualitative analysis, it does not afford an easy nor accurate measurement of the length of the cervix from the external cervical os to the cervical-uterine junction (also described herein as the length of the cervix extending into the vagina) and, therefore, does not provide an accurate assessment of the risk of preterm labor. Despite the use of gloves, vaginal exams always carry with them the risk of transmitting infectious agents, especially to the fetal membranes, the lining and/or muscle of the uterus, or the fetus itself.

Another method involves real-time sonographic evaluation of the cervix. This method provides relatively quick and accurate cervical dimensions. However, it requires expensive equipment, highly skilled operators, as well as skill in interpretation of results, which are all subject to human error. Also, due to the expense of the procedure many women, especially those without proper health insurance, cannot afford to have a sonographic test performed.

It would be beneficial if there were an instrument a practitioner could use to measure the cervix quickly and accurately, and with little material expense. Although there are several instruments available for determining various dimensions of the uterus, there is no suitable instrument for measuring the length of the cervix in the fornix vaginae. For example, U.S. Pat. No. 4,016,867 describes a uterine caliper and depth gauge for taking a variety of uterine measurements, which although useful for fitting an intrauterine contraceptive device, is not capable of measuring the length of the cervix in the fornix vaginae due to interference by the caliper's wings. In fact, similar devices described in U.S. Pat. Nos.: 4,224,951; 4,489,732; 4,685,747; and 5,658,295 suffer from similar problems due to their use of expandable wings or divergable probe tips. These devices are also relatively sophisticated, making them expensive to manufacture and purchase. U.S Pat. No. 3,630,190 describes a flexible intrauterine probe, which is particularly adapted to measuring the distance between the cervical os and the fundus of the uterus. The stem portion of the device has a plurality of annular ridges spaced apart from each other by a predetermined distance, preferably not more than one-half inch apart. However, this device is not adapted for accurately measuring the length of the cervix in the fornix vaginae because of the lack of an appropriate measuring scale and a stop for automatically recording the measurement.

Accordingly, there is currently no commercially available, quick, inexpensive as well as accurate device to assess the risk of preterm labor by measuring the length of the cervix in the fornix vaginae. Therefore, many women at risk for preterm labor may be unaware of the risk to their pregnancy and their unborn child. If such a device were available, many more women would be better informed about the course of their pregnancy and would then be able to make better choices about becoming pregnant at all, or about managing their pregnancy to reduce the risk of preterm labor and injury to the unborn child.

Thus, there exists a need for a simple and inexpensive device that can be used to determine the length of the cervix in the fornix vaginae and, thus, predict the risk of preterm labor, as well as other conditions. There is also a need for such a device that can measure the dilation of the cervix uteri, to provide an overall assessment of the cervix and to determine the particular stage of labor. Ideally, the device should be adapted for use by a physician or obstetrician or even a trained nurse in the doctor's office or clinic. Preferably, the device should be disposable or capable of being sterilized. In addition, it is desirable that device record the measurement automatically. The present invention satisfies these needs and provides related advantages as well.

SUMMARY OF THE INVENTION

The present invention provides devices and methods for determining a dimension of a female reproductive organ.

The present invention provides for a device for determining a dimension of a female reproductive organ, such as, e.g., the cervix, and includes a hollow member with a distal end, a proximal end, and a lumen, a measurement member, insertable into the lumen of the hollow member, having a distal portion, a proximal portion, and a measurement scale along the proximal portion, a flange attached to the distal end of the hollow member, and a light element that is oriented to emit light toward the distal end of the measurement member. The measurement scale of the measurement member, in one embodiment, includes a plurality of color-coded incremental markings. In one embodiment of this device, the light element is located within the distal portion of the measurement member. Here, the device also includes a handle attached to the proximal portion of the measurement member and having an interior space, a power source located within the interior space of the handle, and lead wires attached to the power source and extending through the measurement member to electrically couple the light element with the power source. Alternatively, the light element is a light emitting component that is attached to the hollow member using appropriate attachment means, such as, e.g., snap-on clips and the like. With this alternative embodiment, the device may further include an external power source and lead wires to electrically couple the light emitting component of the light element to the power source. This device, in one embodiment, also includes a locking mechanism to fix the position of the measurement member within the hollow member. Here, the hollow member includes an opening on its proximal portion, and a locking mechanism having a collar with an opening for the insertion of a fastening member is placed around the circumference of the hollow member. Also, a fastening member, such as, e.g., a screw, is provided that is inserted into the opening of the collar, into the opening of the hollow member, and into contact with the measurement member in order to engage and secure the position of the measurement member. In another embodiment of this device, the flange includes a body that is offset from the hollow member, a plurality of measurement markings on the body, and an opening through which the measurement member may be advanced. The flange is preferably manufactured from a substantially translucent material. The device may also include an elongated slot that extends lengthwise along a portion of the hollow and a pin on the measurement member that further comprises a protrusion disposed on an internal surface of the hollow member and the measurement member further comprises a flat surface extending lengthwise along the measurement member. Here, the protrusion and the flat surface are capable of being engaged to fix and maintain the position of the measurement member within the hollow member. In another embodiment, the hollow member further comprises an opening on a circumference of the hollow member for the insertion of a fastening member, such as, e.g., a screw, there through, the measurement member further comprises a flat surface extending lengthwise along the measurement member, and a fastening member is provided that is insertable into the opening of the hollow member to engage the flat surface of the measurement member and fix the position of the measurement member within the hollow member. Alternatively, the hollow member further comprises a slot having a first wall and a second wall, the slot extending lengthwise along substantially the entire length of the hollow member, and the measurement member further comprises a protrusion extending into the slot. With this embodiment, the protrusion of the measurement member is capable of being engaged with a wall of the slot to fix the position of the measurement member within the hollow member.

The present invention further provides for a device for determining a dimension of a female reproductive organ that includes a hollow member having a distal end, a proximal end, and a lumen, a measurement member insertable into the lumen of the hollow member and having a distal portion, a proximal portion, and a measurement scale disposed along the proximal portion, a substantially translucent flange attached to the distal end of the hollow member and having a body offset from the hollow member, an opening extends through the slot. The slot and pin prevent excessive rotation of the measurement member within the hollow member, thereby increasing the ease of operation of the device.

The present invention also provides for a device for determining a dimension of a female reproductive organ that includes a hollow member having a distal end, a proximal end, and a lumen, a measurement member having a distal portion, a proximal portion, and a measurement scale along the proximal portion, wherein the measurement member is insertable into the lumen of the hollow member, a flange with a body offset from the hollow member and an opening for advancement of the measurement member there through, wherein the flange is attached to the distal end of the hollow member, and a light element disposed within the measurement member. In one embodiment of this device, the light element is located within the distal portion of the measurement member and at least the distal portion of the measurement member is substantially translucent. Alternatively, the entire measurement member is substantially translucent. In another embodiment, the hollow member includes a plurality of ports at the distal end of the hollow member in order to allow light emitted from the light element to pass through the hollow member. In another embodiment, both the hollow member and the measurement member are both substantially translucent. This device may also include a handle attached to the proximal portion of the measurement member, a power supply housed within the handle, and a plurality of leads electrically coupling the power supply with the light element, wherein the leads extend from the power supply through the measurement member and to the light element. In addition, several embodiments of the device include a self-locking hollow member and measurement member. In one of these embodiments, the hollow member for advancement of the measurement member there through, and a measurement scale on the body, a light element placed within the distal portion of the measurement member, a handle attached to the proximal portion of the measurement member, a power supply housed within the handle, and a plurality of leads electrically coupling the power supply with the light element, wherein the leads extend from the power supply through the measurement member and to the light element. In one embodiment, the measurement member, the flange, and the hollow member are all manufactured from a plastic material. In another embodiment, the measurement member and the hollow member are manufactured from a metallic material. The device may also include a pressure controlling component that includes an outer sleeve surrounding the handle, wherein the outer sleeve has an outer shell with an interior space that includes a proximal region and a distal region, and a resilient element within the proximal region of the interior space. The handle is placed in the distal region of the interior space and distal to the resilient element.

Other objects and features of the present invention will become apparent from consideration of the following description taken in conjunction with the accompanying drawings.

DESCRIPTION OF THE DRAWINGS

FIG. 1 illustrates a device of the present invention having a measurement member, a hollow member, a flange, a locking mechanism, and a pin on the measurement member that travels within a slot on the hollow member.

FIG. 2 illustrates a flange suitable for incorporation with the devices of the present invention.

FIG. 3 illustrates a device as shown in FIG. 1 and further including a detachable light emitting component attached to the circumference of the hollow member.

FIG. 4 illustrates a device of the present invention that includes a light emitting component integrated into the measurement member and located in the distal portion of the measurement member, and a handle that includes a power source for the light component.

FIG. 5 illustrates a device of the present invention having another embodiment of a locking mechanism.

FIG. 6a(i) is a cross-sectional view of a device of the present invention that includes a hollow member and a measurement member having shapes configured for fixing the position of the measurement member without the need for an additional locking mechanism.

FIG. 6a(ii) is a cross-sectional view of the device shown in FIG. 6a(i) showing a locked position of the hollow member and the measurement member.

FIG. 6b is a cross-sectional view of a device of the present invention incorporating a self-locking feature that includes a slot on the hollow member and a protrusion on the measurement member designed to engage a side wall of the slot in order to fix the position of the measurement member.

FIG. 6c is a cross-sectional view of a device of the present invention incorporating a self-locking feature that includes an opening on the hollow member, a fastening member inserted into the opening, and a flat face on the measurement member, wherein the fastening member is inserted into the opening and engages the flat face to fix the position of the measurement member.

FIG. 6g(i) is a cross-sectional view of a device of the present invention incorporating a self-locking feature that includes an opening on the hollow member, a fastening member inserted into the opening, and two flat faces on the measurement member.

FIG. 6g(ii) is a cross-sectional view of the device shown in FIG. 6g(ii) along the 6g(i).

FIG. 8 is a top plan view of another device of the present invention.

FIG. 8a is a cross-sectional view of the device shown in FIG. 8 along the line 8A—8A.

FIG. 8b is a cross-sectional view of the device shown in FIG. 8 along the line 8B—8B.

FIG. 8c is a side view of the device shown in FIG. 8.

FIG. 8d is a side view of a measurement member of the device shown in FIG. 8. shown in FIG. 8.

DETAILED DESCRIPTION

Figure 6D:
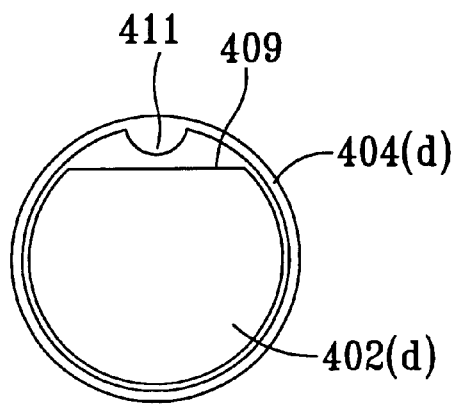
FIG. 6d is a cross-sectional view of a device of the present invention incorporating a self-locking feature that includes a protrusion on the inner wall of the hollow member and a flat face on the measurement member, wherein the protrusion engages the flat face to fix the position of the measurement member.

The present invention provides various devices and methods for determining dimensions of female reproductive organs. For example, the device is particularly adapted for determining the length of the cervix in the fornix vaginae, which, as described above, is related to the risk of preterm labor in an individual. The device is also suited for determining the dilation of the cervix uteri, for predicting the risk of preterm labor or the particular stage of delivery. It is, however, contemplated herein, and also understood by those skilled in the art, that the invention can be used not only for determining various dimensions of female reproductive organs. For example, the invention is usable for determining the dimension of any body cavity or passageway where such a device would be insertable, such as a vagina, uterus, mouth, throat, nasal cavity, ear channel, rectum, and also to any cavity created and opened by surgery, for example, during chest, abdominal or brain surgery. The device is also preferably fabricated from relatively inexpensive materials and the measurement is quick to perform. Thus it allows the practitioner to repeat the test over time and therefore to more closely monitor a woman's pregnancy and risk for preterm labor. It is also contemplated that the device records the various measurements automatically, where the only input required by the practitioner is the proper insertion of the device into the body cavity or passageway. This is accomplished by the use of the flange to stop progression of the hollow member of the device while still allowing the measurement member to be advanced within the body.

As used herein the term "distal" refers to the end or portion of a device of the present invention, or a component thereof, that is adapted to be inserted first into a body cavity or passageway. As such, it will be that part of a device of the present invention furthest from the user while the device is inserted and progressed within the body cavity. Conversely, as used herein, the term "proximal" refers to the end or portion of the device nearest the user while the device is being inserted and progressed within the body cavity.

Turning to FIG. 1, a measuring device 100 of the present invention is illustrated. Measuring device 100 includes an elongated hollow member 104 having a distal region with a distal end, a proximal region with a proximal end, and a lumen extending between the distal and proximal ends. An elongated measurement member 102 is provided and is designed to be inserted into the hollow member 104, and specifically into the lumen of the hollow member 104. The measurement member 102 is elongate in shape and has a proximal region with a proximal end and a distal region with a distal end. The measurement member 102 is capable of being progressed coaxially within hollow member 104 both proximally and distally. In the illustrated embodiment of measuring device 100, attached to the proximal end of the measurement member 102 is a handle 112. In one embodiment, the handle 112 is molded from the same material as the measurement member 102. Suitable materials and methods for the manufacture of the devices of the present invention are discussed herein. Alternatively, the handle 112 is a rubber or foam component that is fitted on to and over the proximal end of the measurement member 102.

A measurement scale 118 is disposed along the proximal portion of the measurement member 102. As used herein, the "measurement scale" refers to any number of a series of visual markings on the measurement member 102 at or near the proximal end, which relate a measurement or distance. In a particularly preferred embodiment, the measuring scale 118 includes a plurality of millimeter (mm) incremental markings and a plurality of centimeter (cm) incremental markings. As illustrated in FIG. 1, the measurement scale 118 includes relatively larger markings at 1, 2, 3, 4, and 5 cm in addition to a plurality of millimeter incremental markings between the centimeter markings. Further, a critical mark 120 is preferably present at approximately 2.5 cm. in one embodiment, the critical mark 120 is presented in a different color, such as, e.g., a red color, relative to the other incremental markings of the measurement scale 118. The critical mark 120 is used to quickly notify a user of device 100 that a particular cervix length represents a greater risk of preterm delivery relative to longer cervix lengths. In another embodiment of the device 100, the measurement scale 118 is coded into a plurality of regions. For example, in one implementation of this embodiment, the incremental markings less than 2 cm are coded in a first color, such as, e.g., red, the incremental markings from 2 to 3 cm are coded in a second color, such as, e.g., yellow, and the incremental markings from 3 to 5 cm are coded in a third color, such as, e.g., green. In this embodiment, the measurement scale 118 is color-coded into three regions that each visually represent the relative risks of preterm delivery for a cervix length falling within the respective region. In the above described example, for instance, the red zone indicates a shorter cervix, and therefore a higher risk of preterm delivery, than the yellow zone, which indicates a cervix length that reflects a higher risk of preterm delivery than the green zone. The measurement scale 118 is capable of being coded into regions based upon other distinguishing marks also, such as, e.g., a first region having a first type of marking for the measurement increments, a second region having a second type of marking for the measurement increments, and a third region having a third type of marking for the measurement increments. In other embodiments of device 100, the incremental markings are in English measurements, such as inches and increments thereof, rather than the metric increments previously discussed.

As illustrated, the device 100 preferably includes a slot 114 oriented along the length-wise axis of hollow member 104. Additionally, measurement member 102 includes a pin 116 disposed distally from the measurement scale 118. In operation, measurement member 102 is placed within hollow member 104 such that pin 116 protrudes through slot 114. As a result, measurement member 102 is slidable within hollow member 104 while the rotation of measurement member 102 within hollow member 104 is significantly reduced.

In another embodiment of device 100 designed to reduce the amount of rotation of measurement member 102 while progressed within hollow member 104, the measurement member 102 and hollow member 104 are not circular in shape. For example, both the measurement member 102 and hollow member 104 may be rectangular, octagonal, square, or another shape having at least one angle such that any rotation of the measurement member 102 within hollow member 104 is substantially reduced and prevented by the angles of the measurement member 102 and hollow member 104. A non-circular measurement member 102 and hollow member 104 may additionally include slot 114 on the hollow member 104 and pin 116 on the measurement member 102 to further decrease the amount of rotation between the two members.

Attached to the distal end of hollow member 104 is a flange 106 that is shaped for non-abrasive contact with tissue. As seen in FIG. 1 and FIG. 2, which is an illustration of device 100 along the line 2—2, the flange 106 is preferably flat and spherically or conically shaped. Alternatively, however, the flange 106 may be any other non-abrasive shape to reduce irritation and scraping of the cervical canal, fundus of the vagina or perforation of the fundus of the uterus. The main body of flange 106 is also preferably offset from the longitudinal axis of device 100. Additionally, flange 106 includes an opening 105 through which measurement member 102 may be advanced distally after the flange 106 contacts a bodily surface. When the device 100 is used to measure the length of a cervix, the device 100 is advanced into the vagina until flange 106 is placed into contact with the end of the cervix at the external uterine opening. At this point, further forward progress of the hollow member 104 within the cervical canal or further within the body is prevented as a result of the contact between flange 106 and the end of the cervix at the external uterine opening. Since flange 106 is preferably offset from the longitudinal axis of device 100, in one manner of operation optimal for measuring the length of the cervix, flange 106 is placed both in contact with the end of the cervix and also covering the external uterine opening. As a result, device 100 is oriented so that measurement member 102 is still able to be progressed within the fornix, rather than being advanced through the uterus, since the body of flange 106 is, with this method, covering the external uterine opening. Subsequently, measurement member 102 is continued to be advanced through opening 105 of flange 106 until the distal end of the measurement member 102 contacts a wall of the body, such as, e.g., the anterior fornix. The length of the cervix is then measured by observing the position of the proximal end of the hollow member 104 along the measurement scale 118 of the measurement member 102.

In another embodiment of the device 100, the flange 106 further includes a plurality of measurement marks 122 that are, for example, usable for measuring the dilation of the cervix or external uterine opening. Here, the flange 106 is preferably manufactured from a substantially transparent or translucent material, such as plastic, so that the user is able to observe the flange 106 while the flange 106 is placed within the body. After the flange 106 contacts the external uterine opening, the user is able to measure the dilation of the cervix by comparing the size of the external uterine opening with the measurement marks 122 on the flange 106. The measurement marks 122 may be metric, such as, e.g., incremental marks of millimeters, centimeters, or a combination thereof, or in English scale, such as, e.g., inches.

Preferably, the flange 106 is secured to the distal end of the hollow member 104 using a suitable attachment means, such as, e.g., an adhesive. Alternatively, the flange 106 may be formed as an integral component of the hollow member 104.

Referring back to FIG. 1, a locking mechanism 124 is preferably located on the device 100 that allows a user to secure the measurement member 102 within the hollow member 104 after a measurement of a body part, such as, e.g., the length of the cervix, has been taken. The locking mechanism 124 preferably includes a collar 108 disposed around the circumference of the hollow member 104 and a locking knob 110 insertable into the collar 108. In one embodiment, as shown in FIG. 1, the locking knob 110 resembles a fastening member, such as, e.g., a screw, with an enlarged area to facilitate the handling of the locking knob 110. Preferably, the locking knob 110 is ergonomically designed so that it may also be used as a handle during the operation and positioning of the device 100 within the body. The collar 108 preferably includes an opening through which the locking knob 110 is capable of being inserted. Additionally, in this embodiment, the hollow member 104 also includes an opening through which the locking knob 110 is inserted after the locking knob 110 is inserted into the collar 108. For example, after a measurement of a body part is taken with the device 100, a user may lock the position of the measurement member 102 within the hollow member 104, and therefore the position of the proximal end of the hollow member 104 along the measurement scale 118 of the measurement member 102, by ensuring that the openings of the collar 108 and the hollow member 104 are aligned and then inserting the locking knob 110 through both openings simultaneously. The locking knob 110 is then threaded through the collar 108 and the hollow member 104 until the locking knob 110 engages the measurement member 102. Once the locking knob 110 engages the measurement member 102, the locking knob 110 is tightened so that movement of the measurement member 102 proximally or distally within the hollow member 104 is prevented. In another embodiment, rather than having an opening on the hollow member 104 for the locking knob 110, the hollow member 104 includes a deformable region around the circumference of the hollow member 104 at the approximate region where the locking mechanism 124 is placed. Here, continued tightening of the locking knob 110 compresses the deformable region of the hollow member 104, thereby placing pressure against the measurement member 102 at the approximate point of the deformable region. Once the deformable region of the hollow member 104 is sufficiently compressed by the locking knob 110, the measurement member 102 is fixed in place within the hollow member 104. In one embodiment, the deformable region is formed by forming a plurality of slits along the circumference of the hollow member 104 at the approximate location of the deformable region.

Turning to FIG. 3, a device 100 of the present invention is shown that includes a light component 126 secured to the hollow member 104. The light component 126 is capable of being oriented to direct light toward the distal end of the hollow member 104. In operation, the light component 126 provides illumination within the body in order to facilitate the placement of the device 100 within the body. Also, in embodiments of the device 100 where the flange 106 includes a plurality of measurement marks 122, the light component 126 is capable of being oriented to also direct light toward the flange 106, thereby increasing the visibility of the measurement marks 122 on the flange 106 when the device 100 is within the body. As illustrated, the light component 126 includes attachment means 128 used to secure the light component 126 to the hollow member 104. In one embodiment, the attachment means 128 are removable from the hollow member 104. The attachment means 128 may be, for example screws designed for secure insertion into corresponding openings on the hollow member 104, or snap-on clips. When the light component 126 uses snap-on clips as the attachment means 128, the light component 126 may be positioned at various locations along the length of the hollow member 104 and at various positions around the circumference of the hollow member 104. In another embodiment, the light component 126 is an integral part of the hollow member 104. Here, the light component 126 is permanently affixed to the hollow member 104 in a predetermined orientation, such as, e.g., an orientation that directs light substantially toward the distal end of the hollow member 104 and to flange 106, and is not removable from the hollow member 104.

In one embodiment of light component 126, light component 126 is powered using a battery that is disposed within the interior of light component 126. In another embodiment, an external power source is provided in lieu of a battery integrated into the interior of the light component 126. When an external power source is used, lead wires are provided that electrically couple the light component to the external power source. The lead wires preferably include a positive wire, a negative wire, and a ground wire. Alternatively, the lead wires include a positive wire and a negative wire, with one of the wires being grounded at some location outside the body, such as, e.g., near the external power source.

FIG. 4 is a device 200 of the present invention that incorporates a light element 230 as part of the measurement member 202. The device 200 includes a hollow member 204 and a measurement member 202 configured to slide coaxially within the hollow member 204. Measurement member 202 includes a measurement scale 218 on its proximal portion that is substantially the same as measurement scale 118 of device 100. Similarly, device 200 includes a locking mechanism 224 that is substantially the same as locking mechanism 124 of device 100. Further, flange 206 of device 200 is substantially the same as flange 106 of device 100 and is located at the distal end of hollow member 204.

Measurement member 202 of device 200 includes a lumen 216. Additionally, device 200 includes a light element 230 disposed within lumen 216. As illustrated, the light element 230 is located in the lumen 216 in the distal portion of the measurement member 202. In a preferred embodiment, the light element 230 is located at the distal end of the measurement member 202. Light element 230 is a light-emitting component capable of generating light that is directed substantially in a distal direction when the device 200 is placed within the body. Light element 230 may be any suitable light source, such as, e.g., a light-emitting diode, a laser, an incandescent light bulb, a fluorescent substance, or the like. In another embodiment, the light element 230 is an array of individual light-emitting components rather than a single light-emitting component. When an array of individual light emitting components are used instead of a single light emitting component, the light element 230 is capable of continually emitting light in the event one of the array of light emitting components fails during the operation of device 200.

To allow for light to pass there through, measurement member 202 is preferably manufactured of a substantially transparent or translucent material such as plastic. In one embodiment, the entire measurement member 202 is constructed from a substantially transparent or translucent material. In another embodiment, the distal portion of the measurement member 202 is constructed from a substantially transparent or translucent material while the remaining portion of the member 202 is constructed from a substantially opaque material such as a metallic substance.

A set of leads 232a and 232b electrically couple the light element 230 to a power source 214. In a preferred embodiment, one of the leads is a positive electrical wire while the other lead is a negative electrical wire. In one embodiment, the leads 232a, 232b are disposed within the lumen 230 of the measurement member 202. The power source 214 is a component that is capable of providing power to the light element 230, such as, e.g., a battery or the like. As illustrated in FIG. 4, the power source 214 is preferably located at the proximal end of the measurement member 202 and, specifically, housed within a handle 212. The handle 212 is preferably positioned at the proximal end of measurement member 202. The handle 212 has an internal space 222 designed to house the power source 214. The internal space 222 is preferably water tight to prevent damage to the power source 214, a switch 216, or other components that may be disposed therein.

The handle 212 also includes a switch 216 electrically coupled to the power source 214 that enables a user to control the power supplied to the light element 230, as desired. In one embodiment, the switch 216 enables a user to either turn on or turn off the supply of power to the light element 230. Alternatively, the switch enables a user to vary the amount of power supplied to the light element 230, thereby allowing a user to variably dim the light element 230 rather than merely turning it on or off. In the illustrated embodiment, the switch 216 is a toggle or flip switch that may be alternated between a first position and a second position. The first and second positions generally correspond to on and off positions respectively. In another embodiment, the switch 216 is positioned at the proximal end of the handle 212, and is operated by turning the switch 216 in a circular fashion. Alternatively, the switch 216 is a membrane component positioned at the proximal end of the handle 212, and is operated by depressing the membrane.

In an alternative embodiment of device 200, measurement member 202 does not include a lumen 216 but, rather, is a solid member formed of a transparent or translucent material such as plastic. In this embodiment, the material that is used to form measurement member 202 encases both light element 230 and leads 232a, 232b. This is in comparison to the embodiment of device 200 illustrated in FIG. 4 wherein light element 230 and leads 232a and 232b are positioned within a lumen 216. When the device 200 includes a solid measurement member 202 encasing light element 230 and leads 232a, 232b, movement of either light element 230 or leads 232a, 232b within the member 202 is substantially restricted. This embodiment of measurement member 202 may be manufactured by coextruding, from a plastic material, both measurement member 202 and leads 232a, 232b, thereby manufacturing a member 202 with built-in leads 232a, 232b. With the embodiment illustrated in FIG. 4, by comparison, leads 232a and 232b lie freely within lumen 216.

In another embodiment of device 200, hollow member 204 is composed of a substantially transparent or translucent material. When constructed of substantially transparent or translucent material, hollow member 204 enables light emitted from the light element 230 to also be emitted there through. As a result, this embodiment of device 200 enables light element 230 to emit a greater percentage of light to the areas surrounding device 200.

Device 200, in another embodiment, includes a plurality of ports on the distal portion of hollow member 204, such as ports 326 shown in FIG. 5 and to be discussed herein. The ports allow an amount of light to be emitted through the hollow member 204 even when the hollow member 204 is not constructed of a translucent material. For example, a hollow member 204 manufactured from a metallic material or an opaque plastic material will still allow some amount of light to shine there through and onto the areas surrounding the device 200 when hollow member 204 includes a plurality of ports on its distal portion.

Illustrated in FIG. 5 is a device 300 of the present invention. Device 300 includes a hollow member 304 and a measurement member 302 configured to slide coaxially within the hollow member 304. Flange 306, located at the distal end of the hollow member 304, is substantially the same as flange 106 of device 100. Measurement member 302 is substantially similar to measurement member 202 of device 300. For example, measurement member 302 includes a measurement scale 318 along its proximal region.

Also, measurement member 302 includes a light element 330 disposed in the distal portion of measurement member 302 and leads 332a, 332b electrically coupled to the light element 330. In a preferred embodiment, light element 330 is located at the distal end of measurement member 302. Also, light element 330 is a light-emitting component capable of generating light, such as, e.g., a light-emitting diode, a laser, an incandescent light bulb, a fluorescent material, or the like, and may be either a single light-emitting component or an array of light-emitting components.

In one embodiment of measurement member 302, member 302 has a lumen 316 in which light element 330 and leads 332a, 332b are disposed. In another embodiment, measurement member 302 has no lumen, but is solid and manufactured from a substantially transparent or translucent material, such as, e.g., plastic. Here, measurement member 302 encases light element 330 and leads 332a, 332b, reducing the degree of movement of leads 332a, 332b, as compared to the measurement member 302 having a lumen 316 and leads 332a, 332b lying freely within lumen 316. For example, this embodiment of measurement member 302 may be manufactured by being coextruded from a plastic material, and having built-in leads 332a, 332b.

The leads 332a, 332b are preferably a positive electrical wire and a negative electrical wire. Further, the leads 332a, 332b electrically couple light element 330 to a power source 314, with may be, e.g., a battery or the like. As with device 200, the power source 314 of device 300 is preferably located at the proximal end of the measurement member 302 and, specifically, housed within a handle 312. The handle 312 is preferably positioned at the proximal end of measurement member 302. The power source is housed within an internal space 322 of handle 312. A switch 316 on the handle 312 and electrically coupled to power source 314 enables a user to turn on or off the power supplied to light element 330. Alternatively, switch 316 allows a user to vary the level of power supplied to light element 330 rather than merely providing an on or an off setting.

Device 300 includes a locking mechanism 324 that includes a locking knob 310 insertable into a collar 308. The collar 308 is disposed between fixed stops 328a and 328b. Fixed stop 328a is located adjacent to the distal end of collar 308, whereas fixed stop 328b is located adjacent to the proximal end of collar 308. Fixed stops 328a and 328b maintain collar 308 at a fixed position along the length of hollow member 304, i.e., the fixed stops 328a and 328b prevent the collar 308 from moving along the length of hollow member 304. Although collar 308 is fixed in place along the length of hollow member 304 by fixed stops 328a, 328b, the collar 308 is still rotatable around the circumference of hollow member 304. As a result of the rotating aspect of collar 308, manipulation and operation of locking mechanism 324 is facilitated since a user is able to rotate collar 308 to a suitable position while operating device 300. Other than the rotating aspect of locking mechanism 324, locking mechanism 324 operates in substantially the same manner as locking mechanism 124 of device 100. For example, in one embodiment, hollow member 304 includes an opening that is configured for the insertion of the locking knob 310 there through. Further, collar 308 also includes an opening that is capable of being aligned with that opening of the hollow member 304. Therefore, when a user desires to lock the position of measurement member 302 within hollow member 304, the user tightens locking knob 310, while knob 310 is inserted into collar 308 and while the openings of collar 308 and hollow member 304 are aligned. The user continues tightening locking knob 310 until locking knob 310 engages and contacts measurement member 302. As a result, locking knob 310 places pressure on measurement member 302, thereby substantially preventing proximal or distal movement of the measurement member 302 within hollow member 304. As with locking mechanism 124, an another embodiment of locking mechanism 324 operates by compressing a deformable region on the hollow member 304 located substantially where color 308 is placed on the circumference of the hollow member 304. Here, continued tightening of locking knob 310 exerts pressure on the deformable region, thereby compressing that region and also placing pressure on measurement member 302.

As previously mentioned, device 300 includes a light element 330 that is either disposed within a lumen 316 of measurement member 302 or encased by measurement member 302 when member 302 does not include a lumen 316. The measurement member 302 is constructed, in whole or in part, of a transparent or translucent material in order to allow light emitted from the light element 330 to pass there through. In one embodiment, the entire measurement member 302 is constructed from a substantially transparent or translucent material. In another embodiment, the distal portion of the measurement member 302 is constructed from a substantially transparent or translucent material while the remaining portion of the member 302 is constructed from a substantially opaque material such as a metallic substance.

In the illustrated embodiment, device 300 includes a plurality of ports 326 located on the distal portion of hollow member 304. Ports 326 allow an amount of light to be emitted through hollow member 304 even when hollow member 304 is manufactured from an opaque material, such as, e.g., a metallic substance. When hollow member 304 is manufactured from a metallic material or an opaque plastic material, light emitting from light element 330 will pass through both the measurement member 302, at the transparent or translucent portions of member 302, and through ports 326 of hollow member 304. As a result, ports 326 increase the area surrounding device 300 that is illuminated by light element 330, particularly when hollow member 304 is composed of an opaque material. In an alternative embodiment, the entire body of hollow member 304 is manufactured from a transparent or translucent material, thereby allowing light emitting from light element 330 to pass through substantially the entire length of hollow member 304.

All of the devices of the present invention include alternative embodiments where the position of the measurement member within the hollow member, after determining the length of the bodily part being measured, is capable of being fixed without the use of locking mechanisms 124, 224, or 324. Rather than requiring a separate locking mechanism component 124, 224, or 324, these alternative embodiments of the devices of the present invention include hollow members and measurement members designed to self-lock, i.e., without requiring the separate locking mechanisms of devices 100, 200, or 300. Several devices having self-locking hollow members and measurement members are illustrated in cross-section in FIGS. 6a–f. The devices in FIGS. 6a–f incorporate hollow members and measurement members incorporating self-locking features that, first, allow for the measurement member to travel longitudinally within the hollow member while also restricting the rotation of the measurement member within the hollow member. Second, the self-locking features of these devices allow for a user to fix the position of the measurement member within the hollow member after a measurement of a body part has been taken.

With the exception of the specifically discussed features, the devices illustrated in FIGS. 6a–f are substantially similar to devices 100, 200, and 300. For example, the devices illustrated in FIGS. 6*a–f* all include an elongated measurement member insertable into an elongated hollow member and capable of being advanced coaxially within the hollow member. A flange is present on the distal end of the hollow member and is operable to stop the progression of the hollow member within a body while enabling continued progression of the measurement member. The measurement member includes a measuring scale located on a proximal portion of the member, in addition to a handle attached to the proximal end of the measurement member. Further, the devices illustrated in FIGS. 6*a–f* may incorporate any of the light emitting components discussed herein. Unlike devices 100, 200, and 300, however, the devices in FIGS. 6*a–d* do not include a separate locking mechanism but, rather, include the integrated self-locking features described herein.

Referring to FIGS. 6*a*(i) and 6*a*(ii), one embodiment of a self-locking device of the present invention, device 400(*a*), is illustrated. As previously discussed, with the exception of a separate locking mechanism, device 400(*a*) includes substantially the same components as the other devices of the present invention, such as device 200 and 300, and is operated in substantially the same manner to obtain a measurement of a dimension of a body part. Device 400(*a*) includes a hollow member 404(*a*) and a measurement member 402(*a*). Hollow member 404(*a*) and measurement member 402(*a*) are substantially similar to hollow member 104 and measurement member 102, with the exception of the shapes of hollow member 404(*a*) and measurement member 402(*a*). Hollow member 404(*a*) and measurement member 402(*a*) are oval in cross-section. Further, measurement member 402(*a*) is slightly flatter in cross-section that hollow member 404(*a*), i.e., has a shorter minor axis 419 than the minor axis 421 of hollow member 404(*a*). As with the other embodiments of the devices of the present invention, measurement member 402(*a*) is still capable of being placed within hollow member 404(*a*) and manipulated coaxially within hollow member 404(*a*). As seen in FIG. 6*a*(i), when a user desires to progress measurement member 402(*a*) within hollow member 404(*a*), device 400(*a*) is operated so that measurement member 402(*a*) is capable of being progressed coaxially within hollow member 404(*a*). For example, to enable to move measurement member 402(*a*) either distally or proximally within hollow member 404(*a*), device 400(*a*) is operated so that the major axis 403 of measurement member 402(*a*) is substantially parallel to the major axis 405 of hollow member 404(*a*). When the major axes 403, 405 are substantially parallel, measurement member 402(*a*) may be advanced within hollow member 404(*a*).

Due to the relative cross-sectional shapes of the members, however, the ability to rotate measurement member 402(*a*) while traveling within hollow member 404(*a*) is restricted. The restriction of the rotation of measurement member 402(*a*) increases the ability to determine the position of the proximal end of hollow member 404(*a*) along the measurement scale of measurement member 402(*a*). Further, the position of measurement member 402(*a*) within hollow member 404(*a*) is capable of being fixed by forcibly rotating measurement member 402(*a*) while a portion of member 402(*a*) is still within hollow member 404(*a*). For example, to fix the position of measurement member 402(*a*) relative to hollow member 404(*a*), a user will forcibly rotate measurement member 402(*a*) so that major axes 403, 405 are no longer in a parallel relationship. As a result, measurement member 402(*a*) will come into contact with the internal walls of hollow member 404(*a*) at at least two points along the internal walls of hollow member 404(*a*). The user then proceeds to exert sufficient force to fix the position of measurement member 402(*a*) within hollow member 404(*a*). Therefore, unlike devices 100, 200, and 300, a separate locking mechanism is not required to fix the position of measurement member 402(*a*) within hollow member 404(*a*). Alternative embodiments of device 400(*a*) are capable of utilizing different cross-section shaped measurement members 402(*a*) and hollow member 404(*a*) but having major axes 403, 405 that, when in substantial parallel relationship, enable measurement member 402(*a*) to be manipulated within hollow member 404(*a*) and, when displaced from a substantial parallel relationship, result in the fixation of measurement member 402(*a*) within hollow member 404(*a*).

Referring to FIG. 6*b*, another embodiment of a self-locking device of the present invention, device 400(*b*), is illustrated. Device 400(*b*) includes a hollow member 404(*b*) having a slot 413 defined by side walls 413*a* and a measurement member 402(*b*) having a protrusion 415. With the exception of a separate locking mechanism, device 400(*b*) includes substantially the same components as the other devices of the present invention, such as device 200 and 300, and is operated in substantially the same manner to obtain a measurement of a dimension of a body part. As with the other devices of the present invention, measurement member 402(*b*), during operation of device 400(*b*), is placed within, and in coaxial alignment with, hollow member 404(*b*) to allow measurement member 402(*b*) to be manipulated proximally and distally within hollow member 404(*b*). Slot 413, in a preferred embodiment, extends length wise, and for substantially the entire length, of hollow member 404(*b*). In another embodiment, slot 413 extends longitudinally along the distal portion of hollow member 404(*b*) for at least a length that is substantially equivalent to the length of the measurement scale on the proximal portion of the measurement member 402(*b*). Protrusion 415 of measurement member 402(*b*), in one embodiment, is a single protrusion located at one position on measurement member 402(*b*). In another embodiment, protrusion 415 is a protrusion that extends length wise along substantially the entire length of measurement member 402(*b*). In the embodiment where slot 413 extends longitudinally along the distal portion of hollow member 404(*b*) for at least a length that is substantially equal to the length of the measurement scale, protrusion 415 is preferably a single protrusion located on the distal portion of measurement member 402(*b*).

While manipulating measurement member 402(*b*) within hollow member 404(*b*), protrusion 415 is oriented so that it lies within slot 413. The positioning of protrusion 415 within slot 413 prevents undesired rotation of measurement member 402(*b*) within hollow member 404(*b*) while a body part is being measured. After measuring a bodily part using measurement member 402(*b*), the position of member 402(*b*) within hollow member 404(*b*) is capable of being fixed by rotating measurement member 402(*b*) in order to forcibly engage protrusion 415 against a side wall 413*a* of slot 413. This is accomplished by, for example, continuing to rotate measurement member 402(*b*) until protrusion 415 physically contacts a side wall 413*a* and then continuing to apply rotational pressure in that direction in order to force at least a portion of protrusion 415 beyond slot 413, i.e., at least a portion of protrusion 415 is forced under a side wall 413*a*. Consequently, the position of measurement member 402(*b*) becomes fixed within hollow member 404(*b*) without requiring a separate locking mechanism.

FIG. 6*c* illustrates another embodiment of a self-locking device of the present invention, device 400(*c*). Device 400(*c*) includes a hollow member 404(*c*) and a measurement member 402(c). Hollow member 404(c) includes an opening 417 through which a fastening member 407 may be inserted. As with the other fastening members of the other devices discussed herein, fastening member 407 may be, e.g., a screw. Measurement member 402(c) includes a flat face 409 that preferably extends the length of the member 402(c). In another embodiment, flat face 409 extends longitudinally along the distal portion of measurement member 402(c) for at least a length that is substantially equivalent to the length of the measurement scale on the proximal portion of the measurement member 402(c). With this embodiment, the opening 417 and the fastening member 407 are disposed on the distal portion of the hollow member 404(c).

Like the other devices of the present invention, measurement member 402(c), during operation of device 400(c), is placed within, and in coaxial alignment with, hollow member 404(c). Measurement member 402(c) is then manipulated proximally or distally within hollow member 404(c) in order to determine the length of the body part being measured by observing the location of the proximal end of hollow member 404(c) along a measurement scale on the proximal portion of measurement member 402(c). With the exception of a separate locking mechanism, device 400(c) includes substantially the same components as the other devices of the present invention, such as device 200 and 300, as is operated in substantially the same manner to obtain a measurement of a dimension of a body part.

During operation, fastening member 407 is inserted into opening 417 of hollow member 404(c). While a measurement is being taken, the position of fastening member 407 within opening 417 restricts the ability to rotate measurement member 402(c) within hollow member 404(c). After a measurement is taken, the position of measurement member 402(c) within hollow member 404(c) is fixed by further tightening fastening member 407 until it contacts the flat face 409 of measurement member 402(c). To facilitate this process, it may be necessary to orient measurement member 402(c) in order for flat face 409 to align with opening 417 of hollow member 404(c). Once fastening member 407 contacts the flat face 409, additional tightening of fastening member 407 exerts pressure upon measurement member 402(c), thereby fixing measurement member 402(c) at that position within hollow member 404(c). As a result, device 400(c) enables a user to fix the measurement member 402(c) at a given position within hollow member 404(c) without requiring the use of a separate locking mechanism, as compared to device 100, 200, and 300.

Referring now to FIG. 6d, another embodiment of a self-locking device of the present invention is shown. Device 400(d) includes a measurement member 402(d) suitable for insertion within a hollow member 404(d). Like measurement member 402(c) of device 400(c), measurement member 402(d) includes a flat face 409 that preferably extends substantially the length of the member 402(d). Hollow member 404(d) includes, on its internal surface, a ridge 411. In one embodiment, ridge 411 extends substantially the entire length of hollow member 404(d). In another embodiment, ridge 411 is a single dimple or protuberance at one location on the internal surface of hollow member 404(d). In another embodiment of device 400(c), flat face 409 extends longitudinally along the distal portion of measurement member 402(d) for at least a length that is substantially equivalent to the length of the measurement scale on the proximal portion of member 402(d). With this embodiment, ridge 411 is a single protuberance disposed at one location on the internal surface of the distal portion of hollow member 404(d).

Device 400(c) includes substantially the same components as devices 200 and 300, with the exception of the locking mechanisms of those devices, i.e., device 400(c) does not require a separate locking mechanism. Device 400(d) is also operated in substantially the same manner of the other devices of the present invention in order to determine a dimension of a body part.

With device 400(d), however, measurement member 402(d), while a dimension of a body part is being determined, is preferably oriented within hollow member 404(d) such that flat face 409 is oriented toward ridge 411. In this manner, measurement member 402(d) is freely slidable coaxially or longitudinally within hollow member 404(d). Additionally, the range of rotational movement of measurement member 402(d) within hollow member 404(d) is limited by the combination of ridge 411 and flat face 409, i.e., ridge 411 restricts the rotation of measurement member 402(d) when ridge 411 contacts an edge of flat face 409.

To fix the position of measurement member 402(d) within hollow member 404(d), after determining the dimension of a body part, such as the length of the cervix, the measurement member 402(d) is rotated so that one edge of flat face 409 contacts ridge 411. Sufficient additional rotational force is then applied to measurement member 402(d) so that flat face 409, and therefore measurement member 402(d), is maintained in a fixed position by ridge 411. As a result, the incorporation of a ridge 411 on the internal surface of hollow member 404(d) and a flat surface 409 on measurement member 402(d) allows a user to fix the position of measurement member 402(d) within hollow member 404(d), thereby preserving the location of the proximal end of hollow member 404(d) along a measuring scale on the proximal portion of measurement member 402(d), i.e., a measurement of a dimension of a body part, without the use of a separate locking mechanism.

Figure 6E:
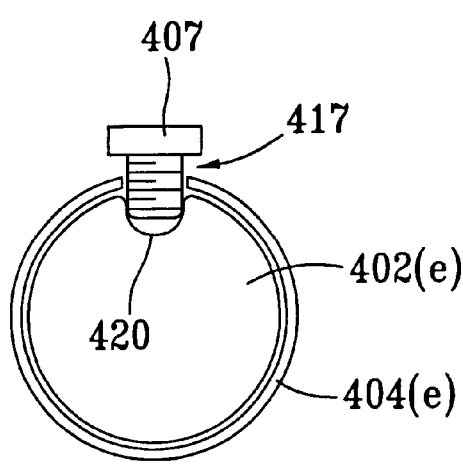
FIG. 6e is a cross-sectional view of a device of the present invention incorporating a self-locking feature that includes an opening on the hollow member, a fastening member, such as, e.g., a screw, inserted into the opening, and an indentation extending longitudinally on the measurement member, wherein the fastening member is inserted into the opening and engages the indentation to fix the position of the measurement member.

Turning to FIG. 6e, another embodiment of a self-locking device of the present invention is shown. Device 400(e) includes a measurement member 402(e) suitable for insertion within a hollow member 404(e). Measurement member 402(e) includes an indentation 420 that extends longitudinally along the length of measurement member 402(e). Indentation 420 preferably extends substantially the length of measurement member 402(e). Hollow member 404(e) includes an opening 417 through which a fastening member 407 may be inserted. Device 400(e) includes substantially the same components as devices 200 and 300, with the exception of the locking mechanisms of those devices, i.e., device 400(e) does not require a separate locking mechanism. Device 400(e) is also operated in substantially the same manner of the other devices of the present invention in order to determine a dimension of a body part.

With device 400(e), however, measurement member 402(e), while a dimension of a body part is being determined, is preferably oriented within hollow member 404(e) such fastening member 407, which is inserted into opening 417 during operation, extends into indentation 420. As a result, measurement member 402(e) is freely slidable coaxially or longitudinally within hollow member 404(e). Further, the range of rotational movement of measurement member 402(e) within hollow member 404(e) is limited by the extension of fastening member 407 within indentation 420.

To fix the position of measurement member 402(e) within hollow member 404(e), after determining the dimension of a body part, such as the length of the cervix, fastening member 407 is tightened such that it engages the bottom surface of indentation 420. Subsequently, fastening member 407 is additionally tightened to ensure that measurement member 402(*e*) is maintained in a fixed position by the engagement of the bottom surface of indentation 420 by fastening member 407. As a result, the incorporation of an indentation 420 on measurement member 402(*e*), in combination with a fastening member 407 insertable into hollow member 404(*e*) and capable of being engaged with indentation 420, allows a user to fix the position of measurement member 402(*e*) within hollow member 404(*e*), thereby preserving the location of the proximal end of hollow member 404(*e*) along a measuring scale on the proximal portion of measurement member 402(*e*), i.e., a measurement of a dimension of a body part, without the use of a separate locking mechanism.

Figure 6F:
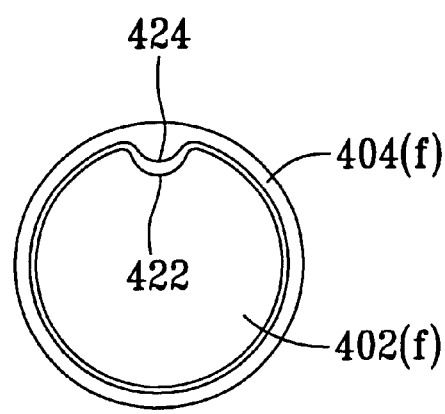
FIG. 6f is a cross-sectional view of a device of the present invention incorporating a self-locking feature that includes a protrusion on the inner wall of the hollow member and an indentation extending longitudinally on the measurement member, wherein the protrusion engages the indentation to fix the position of the measurement member.

Referring now to FIG. 6*f*, another embodiment of a self-locking device of the present invention is shown. Device 400(*f*) includes a measurement member 402(*f*) suitable for insertion within a hollow member 404(*f*). Like measurement member 402(*e*) of device 400(*e*), measurement member 402(*f*) includes an indentation 422 that preferably extends longitudinally along substantially the length of the member 402(*f*). Hollow member 404(*f*) includes, on its internal surface, a protrusion 424. In one embodiment, protrusion 424 extends substantially the entire length of hollow member 404(*f*). In another embodiment, protrusion 424 is a single dimple or detent at one location on the internal surface of hollow member 404(*f*). Device 400(*f*) includes substantially the same components as devices 200 and 300, with the exception of the locking mechanisms of those devices, i.e., device 400(*f*) does not require a separate locking mechanism. Device 400(*f*) is also operated in substantially the same manner of the other devices of the present invention in order to determine a dimension of a body part.

With device 400(*f*), however, measurement member 402(*f*), while a dimension of a body part is being determined, is preferably oriented within hollow member 404(*f*) such that protrusion 424 lies within indentation 422. In this manner, measurement member 402(*f*) is freely slidable coaxially or longitudinally within hollow member 404(*f*). Additionally, the range of rotational movement of measurement member 402(*f*) within hollow member 404(*f*) is limited by the positioning of protrusion 424 within indentation 422.

To fix the position of measurement member 402(*f*) within hollow member 404(*f*), after determining the dimension of a body part, such as the length of the cervix, the measurement member 402(*f*) is rotated so that one edge of indentation 422 contacts protrusion 424. Sufficient additional rotational force is then applied to measurement member 402(*f*) so that indentation 422, and therefore measurement member 402(*f*), is maintained in a fixed position by protrusion 424. As a result, the incorporation of a protrusion 424 on the internal surface of hollow member 404(*f*) and an indentation on measurement member 402(*f*) allows a user to fix the position of measurement member 402(*f*) within hollow member 404(*f*), thereby preserving the location of the proximal end of hollow member 404(*f*) along a measuring scale on the proximal portion of measurement member 402(*f*), i.e., a measurement of a dimension of a body part, without the use of a separate locking mechanism.

Turning to FIGS. 6(*g*)(i) and 6(*g*)(ii), another embodiment of a self-locking device of the present invention, device 500, is shown. FIG. 6(*g*)(ii) is a cross-sectional view of device 500 along the line 6(*g*)(ii). Device 500 includes a hollow member 504 and a measurement member 502. A flange 506 is located at the distal end of hollow member 504 and allows for measurement member 502 to slide there through. Hollow member 504 includes an opening 517 through which a fastening member 507 may be inserted. As with the other fastening members of the other devices discussed herein, fastening member 507 may be, e.g., a screw. Further, fastening member 507, in one embodiment of device 500, is permanently fixed in position within opening 517 and hollow member 504. Measurement member 502 includes a first and second flat face 509*a*, 509*b* that are in opposing relation to each other. The embodiment of device 500 illustrated in FIG. 6*g*(i) includes flat faces 509*a*, 509*b* that extend longitudinally along the distal portion of measurement member 502 for at least a length that is substantially equivalent to the length of a measurement scale 518 on the proximal portion of the measurement member 502. Here, the opening 517 and the fastening member 507 are disposed on the distal portion of the hollow member 504.

Like the other devices of the present invention, measurement member 502, during operation of device 500, is placed within, and in coaxial alignment with, hollow member 504. Measurement member 502 is then manipulated proximally or distally within hollow member 504 in order to determine the length of the body part being measured by observing the location of the proximal end of hollow member 504 along a measurement scale on the proximal portion of measurement member 502. With the exception of a separate locking mechanism, device 500 includes substantially the same components as the other devices of the present invention, such as device 200 and 300. In the embodiment of device 500 shown in FIGS. 6(*g*)(i) and 6(*g*)(ii), the device 500 includes a handle 512 attached to the proximal end of the measurement member 502 that houses a power source 514 and a switch 516 that controls the application of power from the source 514 to a light element 530. The light element 530 is preferably located within the distal portion of measurement member 502 and is electrically coupled to the power source 514 via lead wires 532*a* and 532*b*. Lead wires 532*a* and 532*b* also electrically couple the power source 514 to the switch 516. When a light element 530 is provided, the measurement member 502 and the hollow member 504 are manufactured from a substantially translucent material such as plastic. Alternatively, device 500 is provided without light element 530, power source 514, switch 516, and lead wires 532*a*, 532*b* in order to reduce manufacturing costs of the device 500.

Device 500 is operated in substantially the same manner as, e.g., devices 200 and 300 to obtain a measurement of a dimension of a body part. During operation, fastening member 507 is disposed within opening 517 of hollow member 504. Preferably, measurement member 502 is oriented within hollow member 504 such that one of flat faces 509*a* or 509*b* is positioned toward the fastening member 507. In one embodiment, corresponding markings are provided on the proximal portions of both measurement member 502 and hollow member 504 that, when in alignment, indicate to the user that measurement member 502 is oriented such that one of flat faces 509*a* or 509*b* is positioned toward fastening member 507.

While a measurement is being taken, the position of fastening member 507 within opening 517 restricts the ability to rotate measurement member 502 within hollow member 504. For the embodiment of device 500 where the fastening member 507 is fixed in position within opening 517, after a measurement is taken, the position of measurement member 502 within hollow member 504 is fixed by forcibly rotating the measurement member 502 until one of the ends 510, i.e., not flat face 509*a* or 509*b*, faces fastening member 507. When this is achieved, measurement member 502 is held in place within hollow member 504 by pressure exerted by fastening member 507 on one of the ends of measurement member 502. Alternatively, in an embodiment of device 500 where fastening member 507 is not permanently fixed but, rather, is removable from opening 517, to fix the position of measurement member 502 a user may further tighten fastening member 507 until it contacts a flat face 509a or 509b of measurement member 502. Once fastening member 507 contacts a flat face 509a or 509b, additional tightening of fastening member 507 exerts pressure upon measurement member 502, thereby fixing measurement member 502 at that position within hollow member 504). As a result, device 500 enables a user to fix the measurement member 502 at a given position within hollow member 504 without requiring the use of a separate locking mechanism, as compared to devices 100, 200, and 300.

In another embodiment of the present invention, any of the devices disclosed herein is modified by the addition of a spring-loaded outer sleeve 700 to the handle of that device. The spring-loaded outer sleeve 700 of the present invention, when used in conjunction with one of the devices disclosed herein, allows a constant pressure to be maintained on the device, and specifically on the measurement member, while the device is being advanced within the body. The outer sleeve 700 also prevents undue pressure from being exerted against a bodily surface during the operation of the device by absorbing some of the pressure used to manipulate the device within the body. As a result, outer sleeve 700 reduces the risk of the device puncturing a bodily wall while a measurement of a dimension of a body part is taken with the device.

Figure 7:
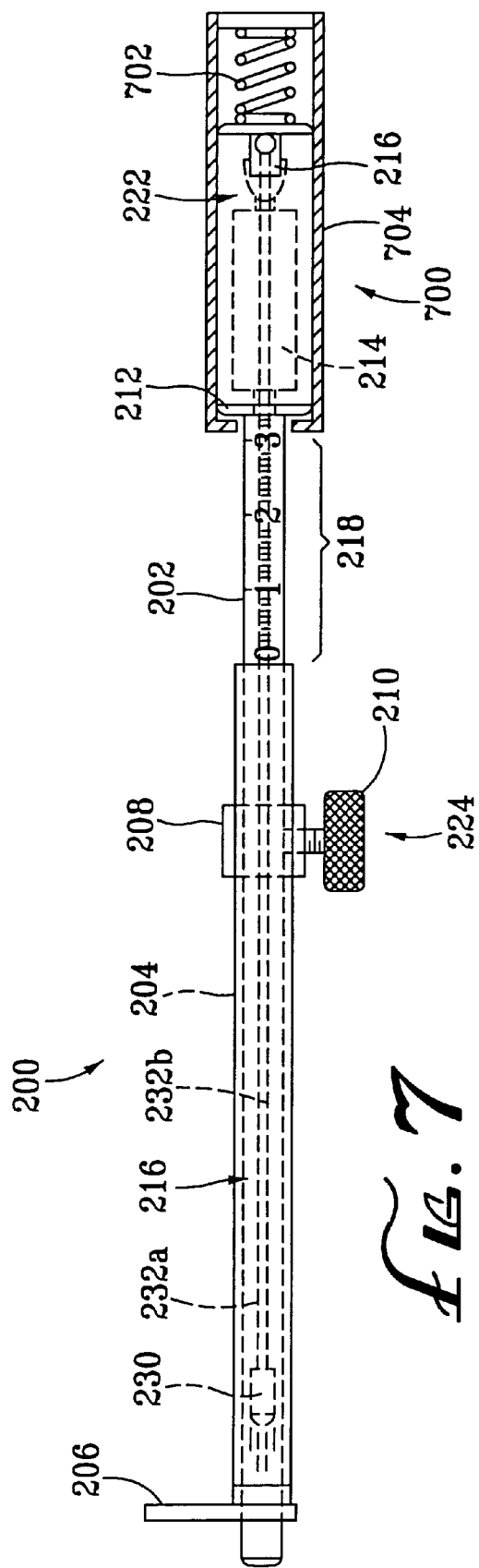
FIG. 7 is a device of the present invention that includes a pressure controlling sleeve surrounding the handle of the device.

As illustrated in FIG. 7, outer sleeve 700 includes an outer shell 704 capable of being placed over a handle of a device of the present invention. As shown in FIG. 7, outer sleeve 700, and specifically outer shell 704, is placed over handle 212 of device 200. Outer sleeve 700 is, however, capable of being placed over any of the other handles of the other devices disclosed herein. Outer shell 704 includes sufficient interior space to accommodate a handle of a device of the present invention as well as a spring element 702, or other resilient structure. In a preferred embodiment, spring element 702 is secured to a proximal wall of the outer shell 704 using a suitable attachment means, such as, e.g., an adhesive.

Preferably, outer shell 704 is placed over, for example, handle 212 of device 200, and handle 212 is situated distally relative to spring element 702. A user will then advance measurement member 202 by manipulating outer sleeve 700. As measurement member 202 is advanced, spring element 702 absorbs any force over a preset level, the level being dependent on the resiliency of the spring element 702 incorporated into outer sleeve 700. Therefore, outer sleeve 700 prevents the force used to advance measurement member 202 from exceeding a present level. Additionally, after the distal end of measurement member 202 contacts a body wall or surface, outer sleeve 700 prevents measurement member 202 from puncturing that surface by absorbing additional force via spring element 702.

In one embodiment, outer sleeve 700 is manufactured from a metallic material, such as, e.g., brass, stainless steel, or the like. In another embodiment, outer sleeve 700 is manufactured from a plastic material. When formed from plastic, outer sleeve 700 may be manufactured using a plastic extrusion technique known in the art. Preferably, the outer sleeve 700 is placed on a handle of a device of the present invention, such as handle 212, at the time the entire device is manufactured and assembled. In one embodiment, the handle is placed into the outer shell 704 and distal relative to the spring element 702. The distal end of the outer shell 704 is then crimped in order to fix the outer sleeve 700 around the handle. In another embodiment, the handle is placed within the outer shell 704 and then a suitable element, such as, e.g., a washer or the like, is affixed over the distal opening of the outer shell 704 using a suitable adhesive or soldering technique in order to maintain the handle within the outer sleeve 700. Alternatively, the outer surface of the handle and the inner surface of the outer shell 704 of the sleeve 700 may contain corresponding threads or grooves, thereby enabling the sleeve 700 to be threaded onto the handle. The outer sleeve 700, in another embodiment, is press fit onto the handle.

Illustrated in FIG. 8 is another embodiment of the present invention, device 800. FIG. 8 is a top plan view of device 800, FIG. 8C is a side view of device 800, and FIG. 8D is a side view of the measurement member 802 of device 800 in isolation. Further, FIG. 8A is a cross-sectional view of device 800 along the line 8A—8A shown in FIG. 8, and FIG. 8B is a cross-sectional view of device 800 along the line 8B—8B shown in FIG. 8. Device 800 includes a measurement member 802 and an outer member 804. Measurement member 802 includes a measurement scale 818 that has a plurality of incremental markings. The incremental markings, in one embodiment of device 800, extend for substantially the entire length of measurement member 802. Outer member 804 includes an open side 805, seen in FIG. 8A, through which measurement member 802, and therefore the measurement scale 818, is visible while the measurement member 802 is disposed within the outer member 804. The open side 805 also includes two extensions 807 that cover an edge of measurement member 802 while member 802 is disposed within outer member 804. Extensions 807 secure measurement member 802 within outer member 804 while simultaneously allowing for movement of member 802 distally and proximally. Measurement member 802 also includes a flange 806 located on its distal end. The flange 806 is preferably a circular shape, a tear-drop shape, or another shape that does not exhibit sharp angles.

In operation, measurement member 802 is placed within and is slidably engaged by outer member 804. Measurement member 802 is capable of being advanced distally and proximally while engaged by outer member 804. In one exemplary use of device 800, device 800 is used to measure the length of the cervix. When used to do so, the device 800 is placed within the vagina and advanced distally until the distal end of outer member 804 comes into contact with the cervical-uterine junction. Then, the measurement member 802 is advanced distally until flange 806 contacts the proximal surface of the cervix, thereby preventing further distal movement of the measurement member 802. A user measures the length of the cervix by observing the location of the measurement scale 818 relative to the proximal end of the outer member 804.

In one embodiment, the position of the measurement member 802 relative to the outer member 804 is maintained by friction between the members. For example, in this embodiment, measurement member 802 is manufactured to fit snugly within outer member 804, but still allowing for movement distally and proximally while engaged within outer member 804. The snug fit between the members enables the maintenance of the position of measurement member 802 within outer member 804 after a measurement is recorded.

Figures 9, 9C, 9D:
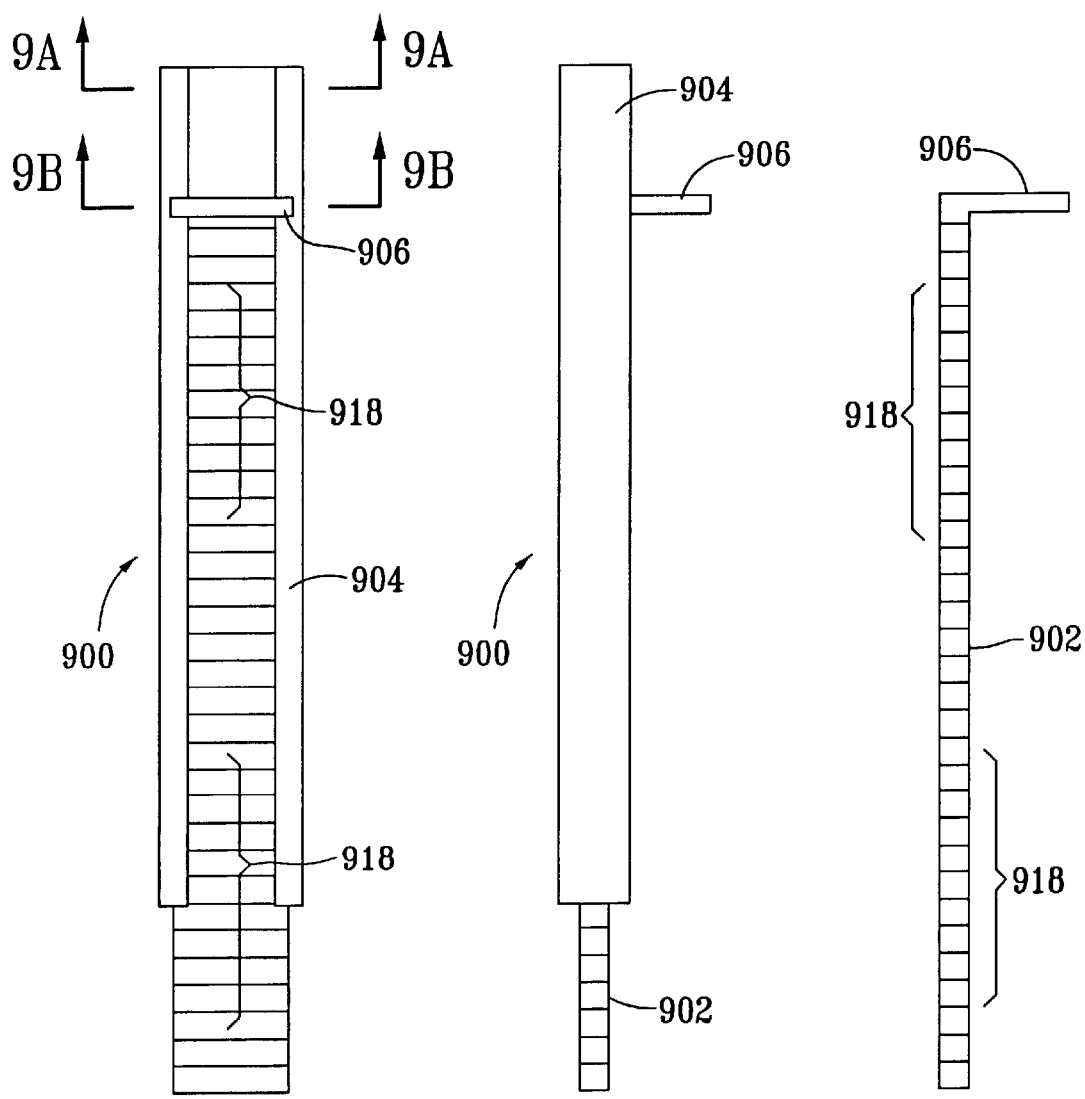
FIG. 9 is a top plan view of another embodiment of a device of the present invention.
FIG. 9c is a side view of the device shown in FIG. 9.
FIG. 9d is a side view of a measurement member of the device shown in FIG. 9.
Figures 9A, 9B:
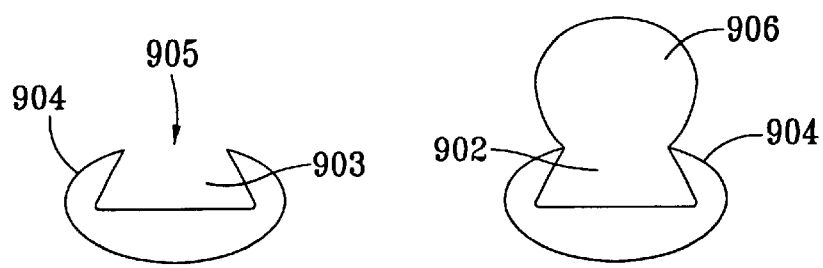
FIG. 9a is a cross-sectional view of the device of FIG. 9 along the line 9A—9A.
FIG. 9b is a cross-sectional view of the device shown in FIG. 9 along the line 9B—9B.

FIG. 9 illustrates another embodiment of a device of the present invention, device 900. FIG. 9 is a top plan view of device 900, FIG. 9C is a side view of device 900, and FIG. 9D is a side view of the measurement member 902 of device 900 in isolation. FIG. 9A is a cross-sectional view of device 900 along the line 9A—9A shown in FIG. 9, and FIG. 9B is a cross-sectional view of device 900 along the line 9B—9B shown in FIG. 9. Device 900 is similar to device 800 in that it includes a measurement member 902, having a measurement scale 918 with a plurality of incremental markings, and an outer member 904. Outer member 904 includes an open side 905, seen in FIG. 9A, through which measurement member 902 and measurement scale 918 is visible while measurement member 902 is disposed within outer member 904. Measurement member 902 also includes a flange 906 located on its distal end that is preferably a circular shape, a tear-drop shape, or another shape that does not exhibit sharp angles. Device 900 is also operable in substantially the same manner as device 800.

Rather than the extensions 807 of device 800 that maintain measurement member 802 within outer member 804, the outer member 904 of device 900 interlocks with measurement member 902. As seen in FIGS. 9A and 9B, outer member 904 engages measurement member 902 without requiring extensions such as extensions 807 of device 800. Here, measurement member 902 includes an angled body. Outer member 904 has angled space 903 configured to accept measurement member 902. Due to the interlocking fit of outer member 904 and measurement member 902, measurement member 902 is capable of being manipulated proximally and distally while disposed within angled space 903 of outer member 904. Also, the interlocking fit of the members allows for measurement member 902 to be slidably engaged by outer member 904. During manufacture of device 900, outer member 904 may be crimped onto measurement member 902.

With regard to materials of manufacture, the devices of the present invention are capable of being formed from either metallic materials or plastic materials. In one embodiment, the devices are manufactured from a metal, such as, e.g., brass, stainless steel, aluminum, or the like, using techniques known in the art. When the devices of the present invention are formed of a metallic material, the devices are capable of being sterilized in order to allow a device to be used repeatedly. Here, the devices are sterilized using an appropriate means, including, e.g., chemical sterilization, thermal sterilization, radiation, and the like, after use in order to allow to extend the lifetime of the device. In another embodiment, the devices of the present invention are formed from a plastic material. With these embodiments, the devices may be extruded from plastic using techniques known in the art. When plastic is used to manufacture the devices, the devices are disposable. Consequently, contamination issues are avoided by virtue of producing devices that are designed to be disposed after use, as compared to the embodiments formed with metal and requiring sterilization. The relative reduced cost of utilizing plastics to manufacture the devices, as opposed to metals, allows for the plastic embodiments of the devices to be intended as disposable units.

The present invention also provides various methods using the devices. For example, the invention provides a method for predicting the risk of preterm labor in an individual by performing the following steps. First, a device that includes a measurement member having a distal region and a proximal region, a hollow member through which the measurement member is inserted and advanced, and a flange engaged with the distal end of the hollow member, is inserted into the vagina. The flange of the device has a surface adapted to contact the cervix at the external uterine opening after the distal end of the hollow member is inserted into the vagina. The device is advanced within the vagina until the flange contacts the cervix at the external uterine opening. At this point, forward progress of the hollow member is prevented. The measurement member is continued to be advanced until the distal region of the measurement member contacts the cervical-uterine junction at the fornix vaginae. Subsequently, the length of the cervix in the fornix vaginae is determined by observing the position of the proximal end of the hollow member along a measurement scale located on the proximal portion of the measurement member. The length of the cervix in the fornix vaginae is inversely related to the risk of preterm labor.

As used herein the term "risk of preterm labor" refers to the risk that an individual will enter labor before the thirty-seventh week of gestation or pregnancy. Using the methods and devices of the present invention, in certain circumstances this risk can be predicted either when the individual is already pregnant or when the individual is not pregnant. When it is possible to evaluate the risk of preterm labor, a patient may gain valuable insight on what may occur during the pregnancy. Also as used herein the term "preterm delivery" is used interchangeably with preterm birth and refers to birth of the fetus as the result of preterm labor. Accordingly, it is contemplated that preterm delivery would occur as the result of preterm labor. Because babies born prematurely may have serious health problems, practitioners try to avoid preterm labor it at all possible. If vaginal bleeding occurs or if the fetal membranes rupture, preterm labor is difficult to stop. If, however, vaginal bleeding does not occur, and the membranes are not leaking amniotic fluid, bed rest with fluid given intravenously helps approximately one in two women. It should also be noted that if the cervix dilates beyond 5 centimeters, labor usually continues until the baby is born. Typically, magnesium sulfate given intravenously stops labor in a majority of cases. Using the devices and methods of the present invention will indicate whether such treatment may be needed in the future.

The invention also provides a method for predicting the risk of miscarriage in an individual. First, a device that includes a measurement member having a distal region and a proximal region, a hollow member through which the measurement member is inserted and advanced, and a flange engaged to the distal end of the hollow member, is inserted into the vagina. The flange of the device has a surface adapted to contact the cervix after the distal end of the hollow member is inserted into the vagina. The device is advanced within the vagina until the flange contacts the cervix, preferably at the external uterine opening. At this point, forward progress of the hollow member is prevented. The measurement member is continued to be advanced until the distal region of the measurement member contacts the cervical-uterine junction at the fornix vaginae. Subsequently, the length of the cervix in the fornix vaginae is determined by observing the position of the proximal end of the hollow member along a measurement scale located on the proximal portion of the measurement member. The length of the cervix in the fornix vaginae is inversely related to the risk of miscarriage.

The present invention also provides methods for predicting the ease of inducing labor. First, a device that includes a measurement member having a distal region and a proximal region, a hollow member through which the measurement member is inserted and advanced, and a flange engaged to the distal end of the hollow member, is inserted into the vagina. The flange of the device has a surface adapted to contact the cervix after the distal end of the hollow member is inserted into the vagina. The device is advanced within the vagina until the flange contacts the cervix, preferably at the external uterine opening. At this point, forward progress of the hollow member is prevented. The measurement member is continued to be advanced until the distal region of the measurement member contacts the cervical-uterine junction at the fornix vaginae. Subsequently, the length of the cervix in the fornix vaginae is determined by observing the position of the proximal end of the hollow member along a measurement scale located on the proximal portion of the measurement member. The length of the cervix in the fornix vaginae is inversely related to the ease of inducing labor.

The invention further provides a method for assessing the fertility of an individual. First, a device that includes a measurement member having a distal region and a proximal region, a hollow member through which the measurement member is inserted and advanced, and a flange engaged to the distal end of the hollow member, is inserted into the vagina. The flange of the device has a surface adapted to contact the cervix after the distal end of the hollow member is inserted into the vagina, includes a measurement scale, and is substantially translucent. Also, the flange is preferably off-set to the side of the hollow member to allow the flange to cover the external uterine opening while also allowing for the further advancement of the measurement member toward the fornix. The device is advanced within the vagina until the flange contacts the cervix, and preferably is placed against the external uterine opening. At this point, forward progress of the hollow member is prevented. The measurement member, however, is continued to be advanced toward the fornix until the distal region of the measurement member contacts the cervical-uterine junction at the fornix vaginae. Subsequently, the length of the cervix in the fornix vaginae is determined by observing the position of the proximal end of the hollow member along a measurement scale located on the proximal portion of the measurement member. Additionally, the dilation of the cervix is measured using the measurement scale on the flange. The length of the cervix in the fornix vaginae is inversely related to the fertility of an individual.

As used herein, the term "fertility" refers to the ability of a female to carry a fetus to the point where it is viable or can survive with the help of medical science, if necessary, when delivered, a female attempting pregnancy, preconceptional evaluation, or procedures involved with infertility treatment. Accordingly, fertility generally refers to the ability of a female to carry a fetus to a normal nine month term, as well as to any other shorter term where the infant would survive on its own or with critical care. By assessing the cervical length and diameter, a practitioner may achieve an appreciation of the fertility of the female, because a risk for preterm labor can be predicted. For example, if the practitioner can determine that a female is at risk for preterm labor and preterm delivery, and that the infant's chances for survival would be small, then the practitioner can advise the female of the risk. Accordingly, the female can make the decision to avoid pregnancy or can, with the assistance of her physician, take steps through diet, rest, and medications to lessen the risk of preterm labor.

As used herein the term "female" refers to a mammalian female, such as a human, horse, dog, cow, pig or monkey. Although the devices and methods are particularly adapted for use in a human female, one skilled in the art understands that they may be used in any female mammal. Accordingly, the devices and methods of the present invention could be used in veterinary medicine, if desired. When used in veterinary medicine, the devices and methods are specifically adapted for the type of animal on which the devices and methods will be used. For example, a device of the present invention adapted for equine use will include a hollow member and a measurement member that is greater in length relative to a device adapted for human use. The hollow member and the measurement member must both be of a sufficient length to enable a veterinarian to measure the length of the cervix, the dilation of the cervix, and the depth of the uterus of a female horse. Since the equine vaginal canal is longer than a human vaginal canal, both the hollow member and the measurement member of the devices of the present invention must accordingly be longer when adapted for equine use.

EXAMPLE I

Cervix Length Measurement

This example provides measurement of the length of the cervix in the vagina in a subject and correlation with reported criteria for determining the risk of preterm delivery. The subject preferably lies in a prone position on her back. The practitioner uses a speculum to first examine the vaginal cavity and to observe the optimum position for placing the device. The practitioner then inserts into the vagina a device that includes a measurement member having a distal region and a proximal region, a hollow member through which the measurement member is inserted and advanced, and a flange engaged to the distal end of the hollow member. The flange of the device has a surface adapted to contact the cervix at the external uterine opening after the distal end of the hollow member is inserted into the vagina. The practitioner next advances the hollow member within the vagina until the flange contacts the cervix at the external uterine opening. At this point, forward progress of the hollow member is prevented. The practitioner then progresses the measurement member through the hollow member until the distal region of the measurement member contacts the cervical-uterine junction at the fornix vaginae. Subsequently, the practitioner determines the length of the cervix in the fornix vaginae by observing the position of the proximal end of the hollow member along a measurement scale located on the proximal portion of the measurement member. Since the length of the cervix in the fornix vaginae is inversely related to the risk of preterm delivery, the practitioner is then able to determine that risk in the patient. The practitioner uses the data provided herein in Table 1, discussed in Iams et al., *N. Eng. J. Med.* 334:567 (1996); which is incorporated by reference herein, in order to determine the relative risk of preterm delivery.

TABLE I

Relative Risk of Preterm Delivery

| Length of cervix (mm) | Percentile | at 24 weeks | at 28 weeks |
| --- | --- | --- | --- |
| 40 | ≦75 | 2 | 2.8 |
| 35 | ≦50 | 2.4 | 3.5 |
| 30 | ≦25 | 3.8 | 5.4 |
| 26 | ≦10 | 6.2 | 9.6 |
| 22 | ≦5 | 9.5 | 13.9 |
| 13 | ≦1 | 14 | 24.9 |

As used herein, the term "relative risk" refers to the likelihood that there will be a preterm delivery when compared to the population which does not have that finding. In this subject, the length of the cervix is determined to be 22 mm. Since the subject is at 24 weeks of gestation, the relative risk for preterm delivery for this subject is 9.5. In other words, this subject has a 9.5 higher risk for preterm delivery than an individual whose cervix is greater than 22 mm in length.

EXAMPLE II

Cervix Dilation Measurement

This example demonstrates the use of the invention disclosed herein to measure the dilation of the cervix uteri in the same subject as in Example 1, to predict the risk for preterm delivery or the particular stage of delivery in a normal pregnancy.

One of the devices of the present invention is used to measure the dilation of the cervix uteri. A physician inserts into the vagina a device that includes a measurement member having a distal region and a proximal region, a hollow member through which the measurement member is inserted and advanced, and a flange engaged to the distal end of the hollow member. The flange of the device has a surface adapted to contact the cervix after the distal end of the hollow member is inserted into the vagina, includes a measurement scale, and is substantially translucent. Also, the flange is preferably off-set to the side of the hollow member to allow the flange to cover the external uterine opening while also allowing for the further advancement of the measurement member toward the fornix. The device is advanced within the vagina until the flange contacts the cervix at the external uterine opening. The physician then measures the dilation of the cervix by comparing the dilation of the cervix with the measurement scale on the flange. Using this procedure, the dilation of the cervix uteri is this subject is found to be 5 cm. Accordingly, the physician advises the subject that delivery is imminent. Since this subject is in her 24$^{th}$ week of pregnancy, this delivery is premature or preterm.

Although the invention has been described with reference to the examples provided above, it should be understood that various modifications can be made without departing from the spirit of the invention. Accordingly, the invention is limited only by the claims.

What is claimed is:

1. A device for determining a dimension of an organ comprising:
   a hollow member having a distal end, a proximal end, and a lumen therebetween,
   a measurement member having a distal portion, a proximal portion, and a measurement scale disposed along the proximal portion, wherein the measurement member is insertable into the lumen of the hollow member,
   a flange attached to the distal end of the hollow member,
   a light element capable of emitting light toward the distal end of the measurement member, and
   a locking mechanism attached to the hollow member, the locking mechanism including a collar having an opening for the insertion of a fastening member there through, the collar being placed around a circumference of the hollow member, and a fastening member inserted through the opening of the collar.

2. A device for determining a dimension of an organ comprising:
   a hollow member having a distal end, a proximal end, and a lumen therebetween,
   a measurement member having a distal portion, a proximal portion, and a measurement scale disposed along the proximal portion, wherein the measurement member is insertable into the lumen of the hollow member,
   a flange attached to the distal end of the hollow member, and
   a light element capable of emitting light toward the distal end of the measurement member,
   wherein the hollow member further comprises an elongated slot extending lengthwise on the hollow member, and the measurement member further comprises a pin extending through the elongated slot.

3. A device for determining a dimension of an organ comprising:
   a hollow member having a distal end, a proximal end, and a lumen therebetween,
   a measurement member having a distal portion, a proximal portion, and a measurement scale disposed along the proximal portion, wherein the measurement member is insertable into the lumen of the hollow member,
   a flange having a body offset from the hollow member and an opening for advancement of the measurement member there through, wherein the flange is attached to the distal end of the hollow member, and
   a light element disposed within the measurement member, wherein the hollow member further comprises a plurality of ports at the distal end of the hollow member.

4. A device for determining a dimension of an organ comprising:
   a hollow member having a distal end, a proximal end, and a lumen therebetween,
   a measurement member having a distal portion, a proximal portion, and a measurement scale disposed along the proximal portion, wherein the measurement member is insertable into the lumen of the hollow member,
   a flange having a body offset from the hollow member and an opening for advancement of the measurement member there through, wherein the flange is attached to the distal end of the hollow member,
   a light element disposed within the measurement member,
   a handle attached to the proximal portion of the measurement member,
   a power supply housed within the handle, and
   a plurality of leads electrically coupling the power supply with the light element, wherein the leads extend from the power supply through the measurement member and to the light element.

5. A device for determining a dimension of an organ comprising:
   a hollow member having a distal end, a proximal end, and a lumen therebetween,
   a measurement member having a distal portion, a proximal portion, and a measurement scale disposed along the proximal portion, wherein the measurement member is insertable into the lumen of the hollow member,
   a flange having a body offset from the hollow member and an opening for advancement of the measurement member there through, wherein the flange is attached to the distal end of the hollow member,
   wherein the hollow member further comprises a protrusion disposed on an internal surface of the hollow member, and the measurement member further comprises a flat face extending lengthwise along the measurement member, wherein the protrusion and the flat face are capable of being engaged to fix a position of the measurement member within the hollow member.

6. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, a flange having a body offset from the hollow member and an opening for advancement of the measurement member there through, wherein the flange is attached to the distal end of the hollow member, wherein the hollow member further comprises a protrusion disposed on an internal surface of the hollow member, and the measurement member further comprises an indentation extending longitudinally along the measurement member, wherein the protrusion and indentation are capable of being engaged to fix a position of the measurement member within the hollow member.

7. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, a flange having a body offset from the hollow member and an opening for advancement of the measurement member there through, wherein the flange is attached to the distal end of the hollow member, and a fastening member insertable into an opening of the hollow member to engage a flat face of the measurement member and fix a position of the measurement member within the hollow member, wherein the hollow member further comprises an opening on a circumference of the hollow member for the insertion of the fastening member there through, and the measurement member further comprises a flat face extending lengthwise along the measurement member.

8. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, a flange having a body offset from the hollow member and an opening for advancement of the measurement member there through, wherein the flange is attached to the distal end of the hollow member, and a fastening member insertable into an opening of the hollow member to engage an indentation of the measurement member, wherein the hollow member further comprises an opening on a circumference of the hollow member for the insertion of the fastening member there through, and the measurement member further comprises an indentation extending longitudinally along the measurement member.

9. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, and a flange having a body offset from the hollow member and an opening for advancement of the measurement member there through, wherein the flange is attached to the distal end of the hollow member, wherein the hollow member further comprises a slot having a first wall and a second wall, the slot extending lengthwise along substantially the entire length of the hollow member, and the measurement member further comprises a protrusion extending into the slot, wherein the protrusion is capable of being engaged with a wall of the slot to fix a position of the measurement member within the hollow member.

10. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, and a flange having a body offset from the hollow member, an opening for advancement of the measurement member there through, and a plurality of measurement markings on the body, wherein the flange is attached to the distal end of the hollow member and is manufactured from a translucent material.

11. A device for determining a dimension of an organ comprising:

a hollow member having a distal end, a proximal end, and a lumen therebetween, a measurement member having a distal portion, a proximal portion, and a measurement scale disposed along the proximal portion, wherein the measurement member is insertable into the lumen of the hollow member, a flange having a body offset from the hollow member and an opening for advancement of the measurement member there through, wherein the flange is attached to the distal end of the hollow member, a handle coupled to the proximal portion of the measurement member, and an outer sleeve surrounding the handle, the outer sleeve comprising
an outer shell with an interior space having a proximal region and a distal region, and
a resilient element within the proximal region of the interior space,
wherein the handle is disposed in the distal region of the interior space.

* * * * *